United States Patent [19]

Rogero et al.

[11] Patent Number: 5,479,359
[45] Date of Patent: Dec. 26, 1995

[54] AUTOMATED DATA COLLECTION SYSTEM FOR FUGITIVE EMISSION SOURCES

[75] Inventors: Lawrence R. Rogero, Santa Barbara; Rex G. Trobridge, Costa Mesa; Luis J. Castleman, Goleta; Tracy L. Schneider, Santa Barbara, all of Calif.

[73] Assignee: Metcalf & Eddy, Inc., Wakefield, Mass.

[21] Appl. No.: 32,272

[22] Filed: Mar. 17, 1993

[51] Int. Cl.⁶ .......................... G06F 19/00; G01N 31/00
[52] U.S. Cl. ................ 364/496; 364/550; 422/62; 422/83; 436/3; 248/206.5; 439/38; 439/39
[58] Field of Search .................. 364/550, 551.01, 364/496, 497; 403/DIG. 1; 248/309.4, 206.5; 211/DIG. 1; 439/38, 39, 40, 527; 422/62, 83; 436/3

[56] References Cited

U.S. PATENT DOCUMENTS

| | | | |
|---|---|---|---|
| Re. 31,750 | 11/1984 | Morrow | 364/508 |
| D. 336,634 | 6/1993 | Richardson et al. | D13/164 |
| 3,951,389 | 4/1976 | Porter | 364/481 |
| 3,999,046 | 12/1976 | Porter | 364/506 |
| 4,060,724 | 11/1977 | Heine et al. | 211/DIG. 1 X |
| 4,112,941 | 9/1978 | Larimore | 439/39 X |
| 4,124,840 | 11/1978 | Kobayashi | 340/670 |
| 4,133,034 | 1/1979 | Etter | 364/464.04 |
| 4,156,280 | 5/1979 | Griess | 364/481 |
| 4,231,249 | 11/1980 | Zuckerman | 73/23 |
| 4,266,768 | 5/1981 | Hall | 273/25 |
| 4,352,164 | 9/1982 | Reed et al. | 364/464.04 |
| 4,360,798 | 11/1982 | Swartz et al. | 340/146.3 AG |
| 4,387,297 | 6/1983 | Swartz et al. | 235/462 |
| 4,394,567 | 7/1983 | Schönhuber | 235/375 |
| 4,398,715 | 8/1983 | Hall | 273/25 |
| 4,409,470 | 10/1983 | Shepard et al. | 235/472 |
| 4,460,120 | 7/1984 | Shepard et al. | 235/472 |
| 4,471,218 | 9/1984 | Culp | 235/472 |
| 4,481,467 | 11/1984 | Alexandersen et al. | 439/38 X |
| 4,490,798 | 12/1984 | Franks et al. | 364/550 |
| 4,496,831 | 1/1985 | Swartz et al. | 235/472 |
| 4,526,028 | 7/1985 | Hübner | 73/23 |
| 4,570,057 | 2/1986 | Chadima, Jr. et al. | 235/472 |
| 4,593,186 | 6/1986 | Swartz et al. | 235/472 |
| 4,621,189 | 11/1986 | Kumar et al. | 235/472 |
| 4,628,193 | 12/1986 | Blum | 235/375 |
| 4,668,940 | 5/1987 | Beard et al. | 340/521 |
| 4,670,405 | 6/1987 | Stetter et al. | 73/23.2 |
| 4,673,805 | 6/1987 | Shepard et al. | 235/472 |
| 4,710,616 | 12/1987 | Utley | 235/472 |
| 4,736,096 | 4/1988 | Ushikubo | 235/472 |

(List continued on next page.)

FOREIGN PATENT DOCUMENTS

| | | |
|---|---|---|
| 61-77754 | 4/1986 | Japan . |
| 1-199150 | 10/1989 | Japan . |
| 3-107752 | 5/1991 | Japan . |

OTHER PUBLICATIONS

"Santa Barbara Team's Device Tracks Fugitive Hydrocarbons," *Clarifier, Metcalf & Eddy People, Projects & News*, Apr./May 1992.
*Century OVA 108 Portable Organic Vapor Analyzer—Insturment Manual*, Apr. 1987.

*Primary Examiner*—Ellis B. Ramirez
*Assistant Examiner*—Eric W. Stamber
*Attorney, Agent, or Firm*—Howrey & Simon; C. Scott Talbot; R. Edward Brake

[57] ABSTRACT

An Automated data collection system for fugitive emission sources includes a handheld data terminal formed as a single portable package or integral unit. The data terminal is connected to an organic vapor analyzer (OVA) and an emissions receiving probe. The data terminal includes a display, a keypad, a microprocessor, a memory, a barcode reader and an analog to digital (A/D) converter for converting the emissions signal received from the OVA to a digital representation. The data terminal facilitates immediate on-site repair by providing repair guidance or repair options to the inspector during the inspections process. Front and rear magnets detachably mount the probe to the data terminal. The probe's rear magnet is recessed to matingly receive the unit's projecting rear magnet.

15 Claims, 18 Drawing Sheets

U.S. PATENT DOCUMENTS

| | | | |
|---|---|---|---|
| 4,748,573 | 5/1988 | Sarandrea et al. | 364/551.01 |
| 4,758,717 | 7/1988 | Shepard et al. | 235/472 |
| 4,788,849 | 12/1988 | Yonemura | 73/40.5 A |
| 4,800,512 | 1/1989 | Busch | 235/376 |
| 4,803,632 | 2/1989 | Frew et al. | 364/464.04 |
| 4,816,660 | 3/1989 | Swartz et al. | 235/472 |
| 4,852,025 | 7/1989 | Herpichböhm | 364/551.01 |
| 4,857,713 | 8/1989 | Brown | 235/375 |
| 4,885,707 | 12/1989 | Nichol et al. | 73/660 |
| 4,898,022 | 2/1990 | Yumoto et al. | 73/46 |
| 4,916,441 | 4/1990 | Gombrich | 340/712 |
| 4,935,875 | 6/1990 | Shah et al. | 235/375 |
| 5,099,436 | 3/1992 | McCown et al. | 364/550 |
| 5,099,437 | 3/1992 | Weber | 364/550 |
| 5,206,818 | 4/1993 | Speranza | 364/550 |
| 5,225,996 | 7/1993 | Weber | 364/550 |
| 5,239,486 | 8/1993 | Mortier | 364/551.01 |
| 5,278,571 | 1/1994 | Helfrick | 343/703 |
| 5,295,499 | 3/1994 | Stutz | 135/68 |
| 5,322,021 | 6/1994 | Jackson | 108/44 |
| 5,356,594 | 10/1994 | Neel et al. | 364/497 |

MAIN MENU:

```
                    OVA:999999
SELECT OPTION:

BEGIN INSPECTING
    UPLOAD/DOWNLOAD
```
FIG.12A

INITIALS SCREEN:

```
                    OVA:999999

ENTER INITIALS:
         A*40
```
FIG.12B

COMPONENT SCREEN:

```
22 / 100                        OVA:      3
                    43502

F1- EQUIP: V-1768
F2- TYPE: HAND VALVE
F3- SIZE: 2.00"
F4- COMP: V1768-010-004
F5- LOC: 2" VL, 6' ABOVE GRND UNDER W END OF V1768
F6- PROC: 000A
F7- UNIT: HTU-4

ENTER = MENU              F9 = EXIT
```
FIG.12C

QUESTION SCREEN:

```
                    OVA:999999
ASK EACH QUESTION DOWNLOADED
       ANSWER: LOGICAL
```
FIG.12D

SKIP SCREEN:

```
                    OVA:999999
SCAN THE TAG OF THE
COMPONENT YOU WISH TO
SKIP TO.
```
FIG.12G

OPTIONS SCREEN:

```
22 / 100              OVA:     3
OPTION MENU:
 1- SKIP THIS COMPONENT
 2- SKIP TO NEW COMPONENT
 3- RETAG THIS COMPONENT
 4- ADD NEW COMPONENT
 5- MODIFY THIS COMPONENT
 6- DELETE THIS COMPONENT
```
FIG.12E

RE-TAG SCREEN:

```
                    OVA:999999
    AFIX THE NEW TAG AND
    SCAN IT WHEN DONE.
```
FIG.12H

UP/DOWNLOAD MENU:

```
SELECT OPTION:
    BEGIN UPLOAD NOW
    BEGIN DOWNLOAD NOW
    AUTOMATIC TRANSFER
```
FIG.12F

ADD SCREEN:

```
                    OVA:999999
    AFIX TAG ON NEW
    COMPONENT AND SCAN IT.
```
FIG.12I

OVA SCREEN:

|  | OVA:999999 |
|---|---|
| CHECK FOR DRIPS! IF DRIPPING ENTER DPM  `99`  —THEN— PULL TRIGGER WHEN OVA READING PEAKS | |

FIG.12J

CONFIRM SCREEN:

|  | OVA:999999 |
|---|---|
| OVA : 99999 DRIPS : 99  ARE THESE CORRECT? | |

FIG.12K

REPAIR MENU:

| LEAKING! | OVA:999999 |
|---|---|
| SELECT REPAIR ATTEMPTED: | |
| LIST OF OPTIONS DEPENDENT ON COMPONENT TYPE. | |
|  | F9 = EXIT |

FIG.12L

PART LEAKING MENU:

|  | OVA:999999 |
|---|---|
| SELECT PART LEAKING: | |
| LIST OF OPTIONS DEPENDENT ON COMPONENT TYPE. | |
|  | F9 = EXIT |

FIG.12M

FINAL SCREEN:

|  | OVA:999999 |
|---|---|
| ORG : 99999    MIN : 99999 DRP : 99999    DRP : 99999 (REPAIR) (PART LEAKING) (ADDED, DELETED, MODIFIED) (RETAGGED) | |
| COMMIT TO INSP? | |

FIG.12N

REPAIR MENU:

| 28 / 100 | OVA: 8 |
|---|---|
| REPAIR ATTEMPTED: NO REPAIR MADE INJECTED WITH GREASE TIGHTENED FLANGE TIGHTENED PACKING REPAIRED VALVE PCKNG REPLACED PACKING | |

FIG.12O

AUTOMATED DATA COLLECTION SYSTEM FOR FUGITIVE EMISSION SOURCES

BACKGROUND OF THE INVENTION

The invention relates generally to sensors, and specifically to systems for detecting fugitive emissions.

Federal, state and local air quality compliance regulations have been promulgated to control fugitive emissions from petroleum production, refining and distribution facilities along with petrochemical facilities including refineries, pumping stations, storage facilities, etc. For example, Rule 1173 of the South Coast Air Quality Management District relates to Fugitive Emissions of Volatile Organic Compounds, and has monitoring, record keeping, and reporting requirements. Similarly, Federal Regulations under 40 C.F.R. §60.105 and 60.107 are another emission standard that impose monitoring, recording, and reporting requirements on petrochemical facilities (but for different constituents).

In general, these regulations require that each possible point of escape for hydrocarbons ("release point") in a facility be identified, monitored, and tracked. Thus, each fitting, joint, packing gland, flange, and other possible release point must be monitored and tracked. Leak limits have been established—if emissions from a source exceed the limit, corrective action must be taken. For example, a slight leak, but one that exceeds a leak threshold, may be subject to repair within 14 days of detection, while a massive liquid leak may be subject to immediate repair.

Tracking the leak history of an emission source is important because a favorable leak history may qualify that source for a reduced monitoring schedule, while a poor leak history may dictate that the part be replaced, the joint reformed, or other corrective action taken. In addition, local and federal regulators have the power to issue notices of violations if appropriate record keeping and required emissions levels are not maintained.

The data collection industry has recognized the advantages of the elimination of paper records in favor of electronic data collection systems. U.S. Pat. No. 5,099,437 to Weber ("Weber") discloses an electronic data collection system for monitoring and tracking fugitive emissions. As shown in prior art FIG. 1, Weber employs a portable barcode scanner 10 for reading barcodes tags fixed to a release point and for generating a signal representative of the barcode value scanned. A portable data collector 12 is coupled to the scanner and receives from the scanner the bar code identification signals. A portable organic vapor analyzer ("OVA") 16 analyzes vapors sensed by vapor probe 14, which includes an analog gauge for continuously displaying the sensed vapor concentration. An analog voltage signal representative of the sensed vapor concentration is transmitted from the OVA to the portable data collector, where the signal is convened from analog to digital and stored in memory. The portable data collector also includes a display for displaying the sensed emissions data.

In using the Weber system, at each release point, the inspector first scans the bar code identification tag associated with the release point. The inspector then applies the probe to the release point, observes the vapor concentration as displayed on the probe's gauge, and locks the sensed analog signal from the OVA into the data collector, creating and closing an emission data record.

After completing inspection of the desired release points, the data collector is connected to a main computer 18 and the emission data records are uploaded from the data collector to the main computer. The main computer compares the sensed data to a predetermined criterion, and is passed or failed. The main computer updates the inspection history, issues repair schedules or lists for emissions sources that failed. and generates reports.

Although the system disclosed in Weber is an improvement over earlier manual sensing and recording systems, it has several drawbacks and disadvantages. It has four separate components—the barcode scanner, portable data collector, vapor analyzer, and vapor probe, all of which must be connected together and carried by the inspector. Several lines are required to interconnect the components (a sample collection line from the probe to the OVA and electrical data lines from the OVA to the dam collector, from the scanner to the data collector and from the OVA to the analog meter). Each line has a connection at each end that is a potential failure point. Each electrical connection must also meet stringent safety requirements, such as intrinsically safe standards for Class I, Division I Group A-D hazardous environments.

The number of components and interconnection lines also renders Inspection of release points cumbersome and inefficient. The inspector must first use the scanner to read the identification bar code, then release the scanner and apply the probe to the release point, observing the reading on the probe's meter. Then, the inspector must lock the sensed reading into the data collector. The separate handling and coordination of the different components complicates the inspection process.

Further, the Weber system does not provide the inspector with on-site guidelines or suggestions for possible repairs. Instead, analysis of the data is performed by the main computer 18, which generates repair instructions for each release point based on the results of the analysis. Thus, a second trip to each release point is always required to repair the leaking part. In the interim between the first visit for emissions measurement and the second visit for repair, the release point has continued to release hydrocarbons into the atmosphere.

The assignee of the present application has used an apparatus similar to the Weber system, except that the portable data collector includes a keyboard to permit the inspector to enter dam, and a separate analog-to-digital converter is disposed in-line between the OVA and the dam collector to convert the analog signal from the OVA to a digital signal usable by the data collector.

SUMMARY OF THE INVENTION

The automated dam collection system of the invention overcomes the disadvantages and drawbacks of the prior art by providing a handheld data terminal formed as a single portable package or integral unit. The data terminal is connected to an OVA and an emissions receiving probe that is detachably mounted to the data terminal for easy inspection of components or emissions sources. The data terminal displays for the inspector on a continuous basis the measured hydrocarbon emission level being analyzed by the OVA. The data terminal also provides to the inspector via a visual display immediate on-site repair information or suggestions during the inspections process, allows the inspector to identify the emission source on the component if the initial on-site repair is ineffective, and provides an audible warning tone to the inspector when the OVA reading exceeds a maximum safe level and to assist the inspector in identifying the emission location.

The data terminal includes a display, a keypad, a barcode reader for reading barcode identification tags, a microprocessor for executing commands or a software program, a memory for storing operating software and data, and an analog-to-digital ("A/D") converter for convening the analog emissions signal received from the OVA to a digital representation. All of these components are arranged in the data terminal in a single handheld package. Therefore, both the inspection process and the management of the data collection system has been simplified by combining the various components into a single handheld unit.

To further reduce the number of components that must be handled by the inspector during the inspection process and to allow for one-handed inspection operation, the emissions receiving probe is detachably mounted to the data terminal. Front and rear magnets are provided on one side of the data terminal unit, and a corresponding set of front and rear magnets are provided on the probe body. When the probe is brought near the data terminal unit, the magnetic fields of the corresponding magnets interact to draw the probe into position on the side of the data terminal and hold the probe in place. In this fixed position, the probe tip is disposed in front of the data terminal.

The rear magnet of the data terminal projects outward from the surface of the terminal, while the rear magnet on the probe is recessed into the probe body to matingly receive the terminal's projecting rear magnet. This creates a mechanical stop or physical connection between the terminal and the probe that supplements the magnetic connection provided by the magnets. The projecting magnet and recess provide additional stability to the probe and prevent an accidental bump from completely separating the probe from the data terminal unit. However, a bump that is violent enough to damage the probe will separate the front magnets, allowing the probe to pivot about the rear magnets and away from the object into which it is bumped. The probe may be readily removed from the dam terminal by the application of lateral force to the probe body.

The analog emission gauge of the OVA is eliminated, and instead the analog output signal from the OVA is continuously supplied to the data terminal, where it is convened to digital format and displayed on the terminal's display. The inspector can thus continuously view the measured emission level directly on the data terminal.

To use the data collector, the inspector scans the bar code of the release point to be inspected by pointing the data terminal at the bar code tag and activating a trigger on the data terminal. Then, still holding the data terminal in the same position, the inspector can place the probe tip at the release point, observe the sensed emission level on the terminal's display, and, when the sensed level has steadied, the inspector pulls the trigger a second time to lock the reading into memory. The data terminal compares the OVA reading and a liquid drip rate recorded by the inspector into memory to threshold values to determine if the component needs a repair. If the OVA reading or the drip rate exceeds its respective threshold value, the data terminal unit displays several repair options or repair suggestions to the inspector. The inspector may then perform one of the suggested repairs. If the attempted repair fails to minimize the leak, then the inspector is allowed to select from a list of leak locations to record what part of the component is leaking. By providing immediate repair guidance or suggestions, the data terminal of the invention may reduce the release of harmful fugitive emissions by facilitating the repair of the component on the first trip or inspection.

BRIEF DESCRIPTION OF THE DRAWINGS

FIGS. 12A–12O illustrate screen displays generated by the software.

DETAILED DESCRIPTION

As shown in FIGS. 2–5, automated dam collection system 20 includes a data terminal 22, an emissions probe 24 mounted to data terminal 22, and an OVA 26. The system 20 is used to monitor fugitive emissions from release points such as the flange 28.

Figure 1:
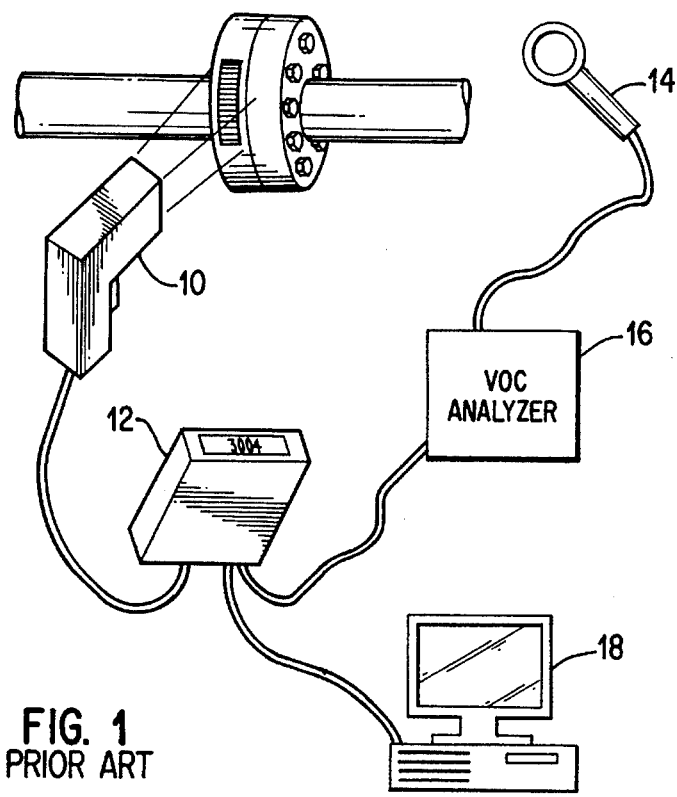
FIG. 1 schematic illustration of the data collection system of Weber.

Probe 24 receives a vapor sample that may include fugitive emissions of volatile organic compounds released from release point 28. A gas line 36 carries the vapor sample from the source 28 to OVA 26. OVA 26 analyzes the vapor sample received from probe 24 and produces an analog signal representative of the concentration of the emission component of interest. For example, the analog signal may be representative of the hydrocarbon content of the vapor sample. OVA 26 may be, for example, a Foxboro Model Century 108 Organic Vapor Analyzer. The Foxboro OVA has two electric signal output ports—one that supplies an analog signal to the OVA's display meter via the sample port of the OVA (as illustrated in the Weber system of FIG. 1). The analog signal received and displayed by the meter is dependent upon the concentration of organic compounds in the sample being analyzed. The second output of the OVA is used to integrate the OVA with a data logger (used in the Weber system for connection to the data collector 12). In the present invention, only the first output source of the OVA is used. The analog signal output by the OVA is transmitted from the OVA to the data terminal 22 via cable 38. Cable 38 connects to analog input terminal 49 of data terminal 22.

The data terminal 22 includes a barcode reader 54 for reading the barcode identification tags 30 located near or affixed to a release point 28 and including unique barcode indicia identifying the release point 28. A character-based display 32 is provided on the data terminal 22 for displaying information to the user, and is preferably a liquid crystal display (LCD). A keypad 34 allows the inspector to input commands and/or information into the data terminal 22. Data terminal 22 also includes a memory 56 for storing information and computer programs, and a microprocessor 50 for executing instructions in the operating software stored in memory. The body of the dam terminal 22 is generally shaped like a pistol, and includes a handgrip 25 with a trigger 27. As shown in trigger function 53 (FIG.5), the trigger 27 may be pulled to activate the laser barcode reader 54 to read in a bar code, or may be pulled to store in memory an OVA reading that has been received by the data terminal from the OVA and converted into a digital representation by an A/D converter.

The data terminal 22 may be based on a device such as the Symbol Technologies, Inc. 3805 Data Collection Terminal ("3805 DCT"), or a similar device. The 3805 DCT which has a barcode reader 54, display 32, keypad 34, memory 56 and microprocessor 50 and an optically coupled communications port to provide data transfer between the data terminal and a main computer. The use of the trigger to activate the barcode reader 54 is a capability that is built into the 3805 DCT, while the feature of recording an OVA reading in memory using the trigger was an additional feature that was added to the 3805 DCT by software programming. The probe mount (magnets, etc.), the A/D converter 52, and the operational software were also added to the 3805 DCT as described herein to produce the data terminal unit 22 of the described embodiment.

The data collection system 20, including the data terminal 22, the sample receiving probe 24, and the OVA 26 operate together to assist in monitoring and identifying components or fugitive emissions sources. In addition, a main computer (not shown) is used to maintain a database of inspection histories, inspection frequencies, dates, repairs, etc., for each component or emissions source. Periodically, information residing on the main computer may be printed out to generate reports on the compliance of each of the components. Before using the data collection system to conduct an inspection, the operational software and component inventory information is downloaded into the data terminal from the main computer.

Figure 2:
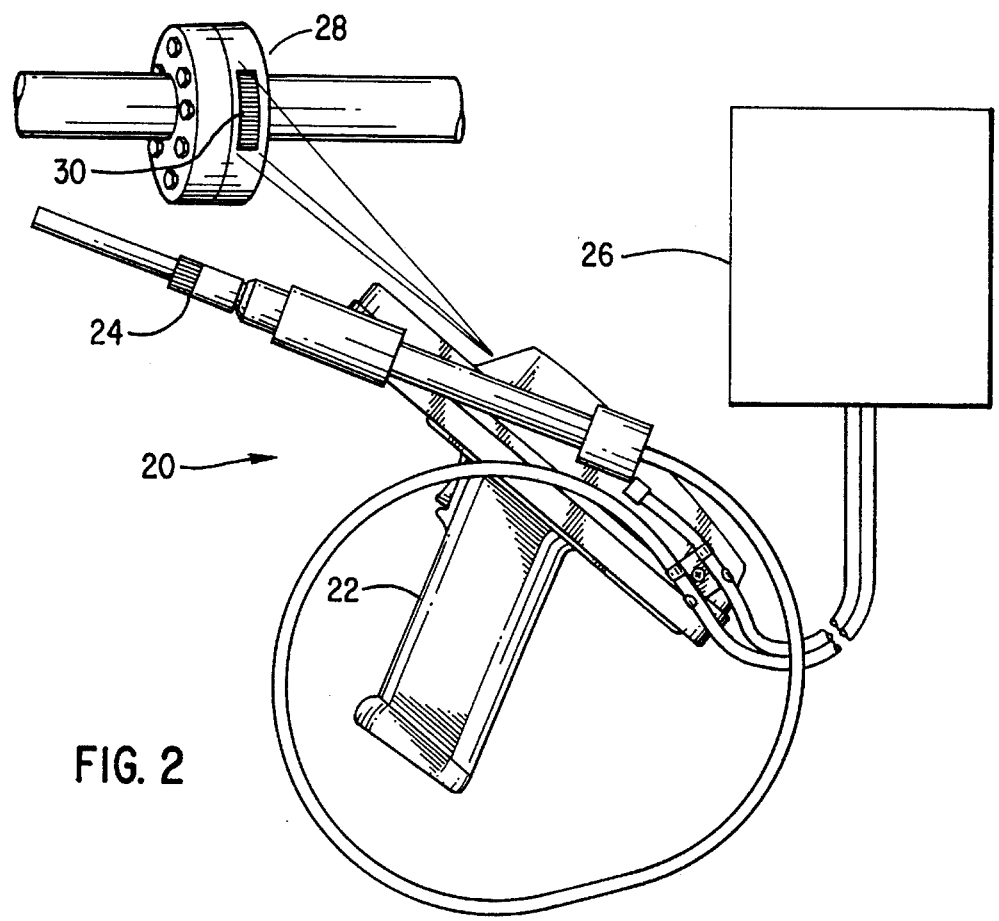
FIG. 2 the automated data collection system constructed according to the principle (the invention.
Figure 3:
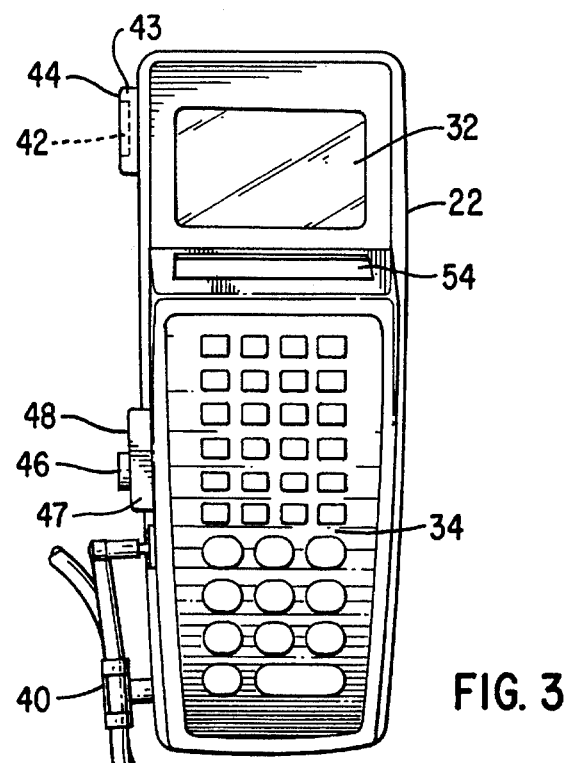
FIG. 3 is a top view of the data terminal shown in FIG. 2, with the probe detached from the data terminal.
Figure 4A:
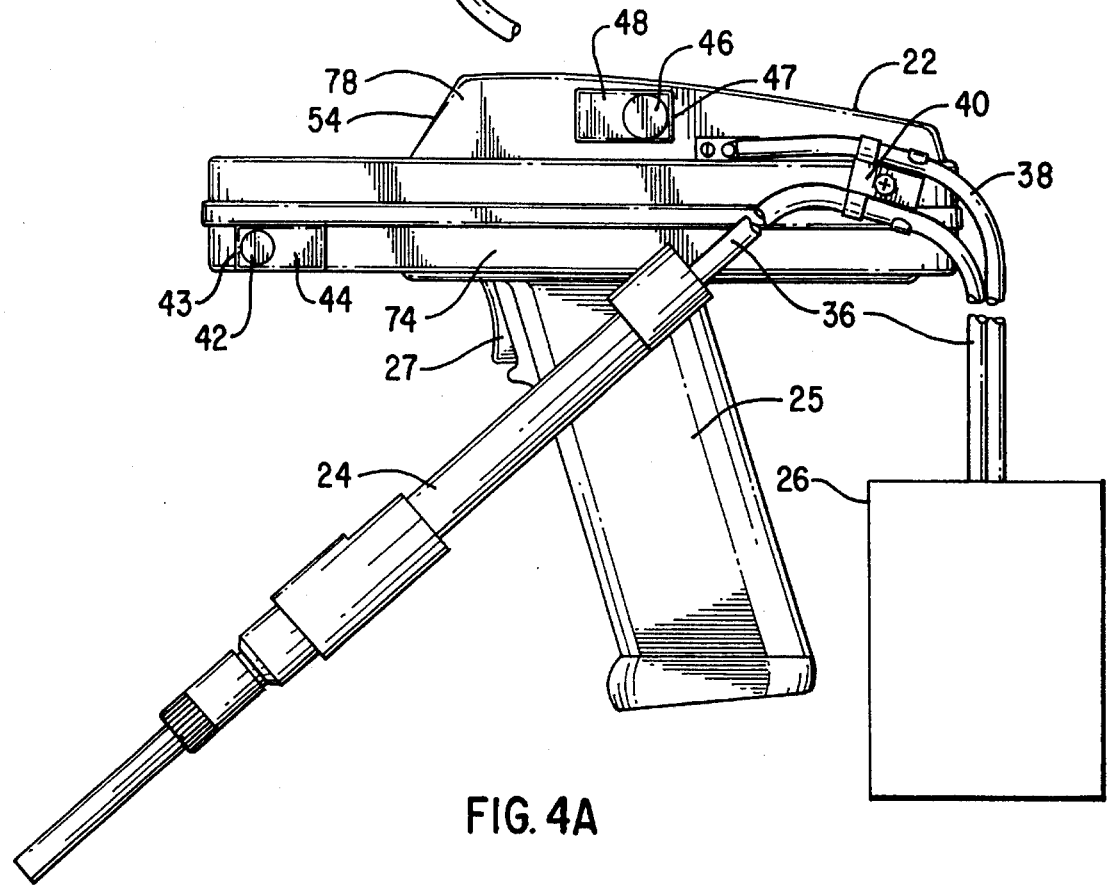
FIG. 4A is a side view of the data terminal shown in FIG. 2, with the probe detached, and the OVA.

As shown in FIGS. 2 and 4A, probe 24 is detachably mounted to the side of data terminal 22. As shown in FIGS. 6–9, probe 24 has a conventional, tubular metal probe tip 66, a tubular handle portion 61, a front mounting portion 63, and a rear mounting portion 65. Gas sample line 36 passes through the interior of handle portion 61 and front and rear mounting portions 63 and 65 and is coupled to the rear extremity of probe tip 66.

Front and rear mounting portions 63 and 65 each have generally planar probe mounting surfaces 59 and 62, respectively, formed thereon. Front probe magnet 58 is mounted in probe mounting surface 59. The upper surface of the front probe magnet 58 is mounted flush with front probe mounting surface 59. Rear probe magnet 60 is recessed below rear probe mounting surface 62.

The data terminal 22 includes front and rear mounting pads 43 and 47, respectively. Each pad is fixed to the side of the terminal by any suitable means such as adhesive or screws. The front and rear mounting pads have generally planar front and rear terminal mounting surfaces 44 and 48, respectively, and have mounted therein front and rear terminal magnets 42 and 46, respectively. Front terminal magnet 42 is mounted so that its upper surface is flush with front terminal mounting surface 44. Rear terminal magnet 46 is mounted so that its upper surface projects outward from the rear terminal mounting surface 48 a distance approximately equal to the distance that the top surface of rear probe magnet 60 is recessed below rear probe mounting surface 62.

Each of magnets 42, 46, 58, and 60 is preferably a cylindrical permanent magnet having a high magnetic field strength. In the present embodiment, the magnets are formed of neodymium-iron-boron. Front magnets 42, 58 are approximately 0.5" (13 mm) in diameter, and 0.25" (6 mm) thick, while the rear magnets 44, 60 are approximately 0.375 "(10 mm) in diameter and 0.25" (6 mm) thick. The magnets can be purchased from magnet suppliers such as All Magnetics of Placentia, Calif. as part numbers ND 143-27 and ND 187-27, respectively. The magnets are disposed so that the north pole of each probe magnet faces the south pole of the corresponding terminal magnet. Thus, when the probe 24 is brought near the data terminal 22 in approximately the correct orientation, the probe and terminal magnets attract each other, drawing the probe 24 into position on the data terminal 22. The planar mounting surfaces mate with each other, providing a stable connection that resists angular displacement of the probe about its longitudinal axis. The relatively large axial distance between the front and rear magnet pairs provide a high resistance to displacement of either end of the probe laterally away from the data terminal.

The terminal mounting pads and the probe mounting surfaces can be formed of any suitable non-magnetic material, such as the organic resin sold under the trade name DELRIN. The magnets can be mounted in the pads and mounting surfaces, such as by adhesive or a set screw that is threaded through the pad and bears against the side of the magnet.

The portion of rear terminal magnet 46 that projects above rear terminal mounting surface 47 fits into the recess above rear probe magnet 60. This mechanical interlock prevents any movement of the rear of the probe either along its axis or vertically perpendicular to its axis. The rear of the probe can be pulled laterally away from the rear of the terminal, but this requires a significant amount of force. The probe is also freely pivotable about the axis of the rear magnet pair. Of course, the rear magnet pair may be arranged so that the rear terminal magnet is recessed, while the rear probe magnet is projecting.

In contrast, the front probe and terminal magnets 58 and 42 are flush with their respective mounting surfaces, and therefore resist displacement in the plane of the mounting surfaces only by their magnetic attraction. The shear force required to separate the magnets along the plane of their faces is significantly less than the axial force required to separate them perpendicular to the plane of their faces. Thus, a relatively small force applied to the probe tip in the plane of the front mounting surfaces can separate the front magnets, pivoting the probe about the axis of the rear magnet pair.

The magnetic and physical mounts allow for one-handed operation of the dam collection system 20, while allowing for convenient removal of the probe from the data terminal 22. For one-handed operation of the system, the probe 24 is mounted to the data terminal 22. However, field use shows that it is not always practical to place the probe into the desired sampling position when it is attached to the data terminal because the configuration of some components does not allow the inspector to inspect the component while simultaneously viewing the OVA reading displayed on the display screen 32. The probe can therefore be readily detached from the dam terminal 22. Therefore, the magnets provide a method of quickly separating the probe from the data terminal while still allowing one-handed operation.

The physical connection at the rear of the probe acts as a mechanical stop and allows the probe to pivot or rotate about the rear magnets when the front magnets are separated. If the probe is struck with sufficient force, such as by dropping the integral probe and data terminal, the magnets allow the probe to separate from the data terminal and thereby prevent damage to the data terminal. However, if the tip of the probe is struck with lesser force, but one sufficient to break the holding force of the front magnets, the rear pair of magnets and mechanical stop will still maintain adequate force to keep the probe attached to the data terminal and prevent the safety hazard of a dangling probe.

It will be apparent to the artisan that the detachable magnetic mounting of the probe to the data terminal can be implemented in many ways other than that described above. For example, each magnet pair at the front and rear mounting points could be replaced by a single magnet and a piece of ferrous material (such as iron). Small electromagnets could be used instead of permanent magnets. A single long bar magnet (on the probe, the data terminal, or both), aligned along the axis of the probe, could be used. Each end of the bar magnet would have a magnetic pole, corresponding to one face of the front or rear cylindrical permanent magnet described above. The rear end of the bar magnet could also incorporate the recessed mounting feature described above.

Sample line 36 is a piece of tubing formed of any suitable material, such as polytetrafluoroethylene, sold under the trade name TEFLON, or an organic resin sold under the trade name VITON. Cable 38 may be any suitable strand of electric data cable, that can remain flexible in a broad range of temperatures and withstand repeated flexing. A suitable cable, is RG-174/N coaxial cable which meets U.S. government standards for miniature 50 Ω coaxial cable. The electric cable 38 and sample line 36 are both covered with heat shrink tubing and the electric cable 38 is also covered with a neoprene covering to protect the electric cable. In addition, to protect the cable 38 and gas sample line 36 from wear and damage, cable 38 and/or line 36 may be enclosed in a suitable wear shroud, such as a braided nylon sleeve.

The cable 38 is connected to the data terminal 22, and thence to the A/D converter 52 via analog input terminal 49. Terminal 49 is preferably an "SMB" type quick connect coaxial terminal, but any suitable connector may be used that is quick-connecting without screws or clamps.

Figure 4B:
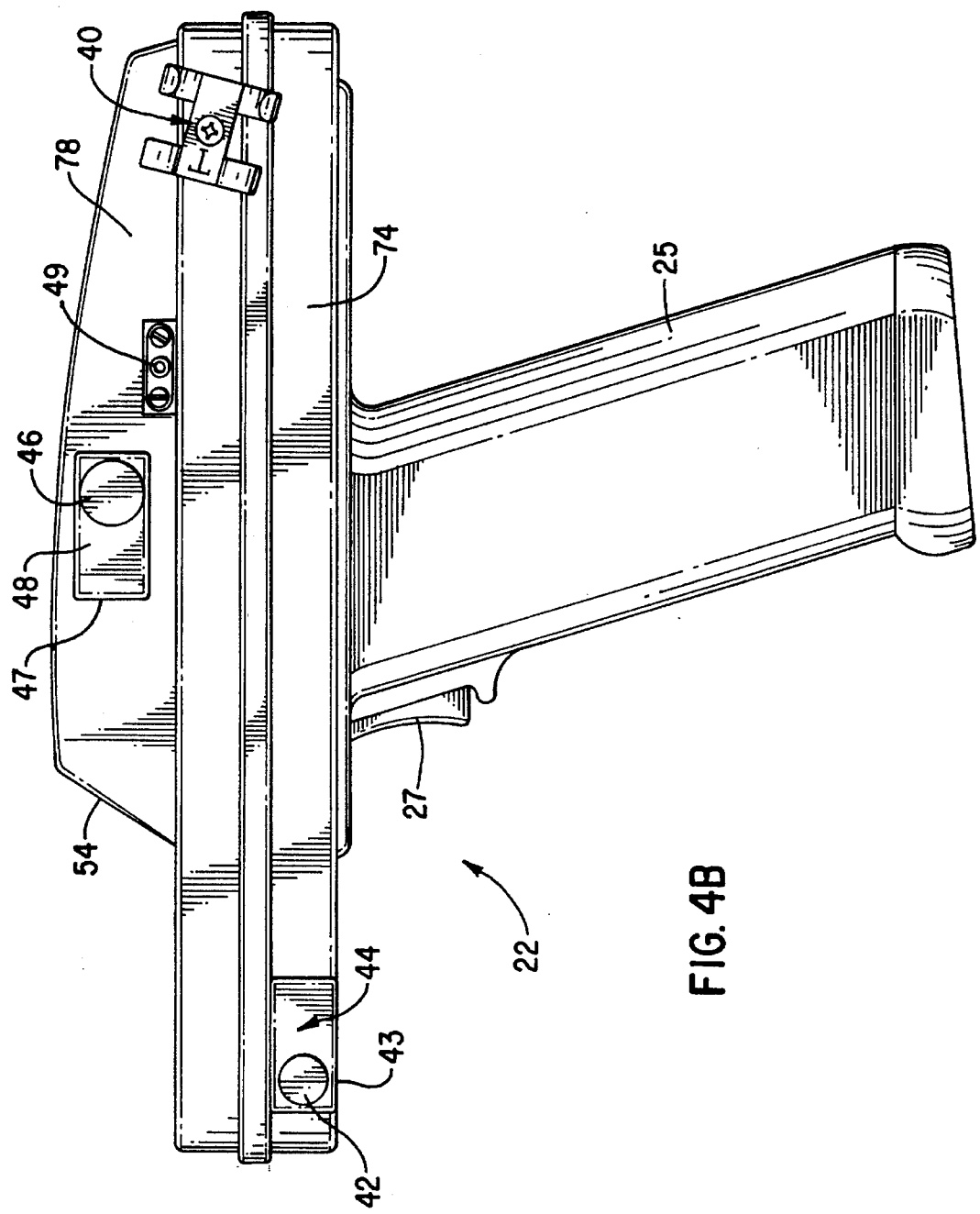
FIG. 4B is a side view of the data terminal shown in FIG. 2, without the probe and OVA.
Figure 10:
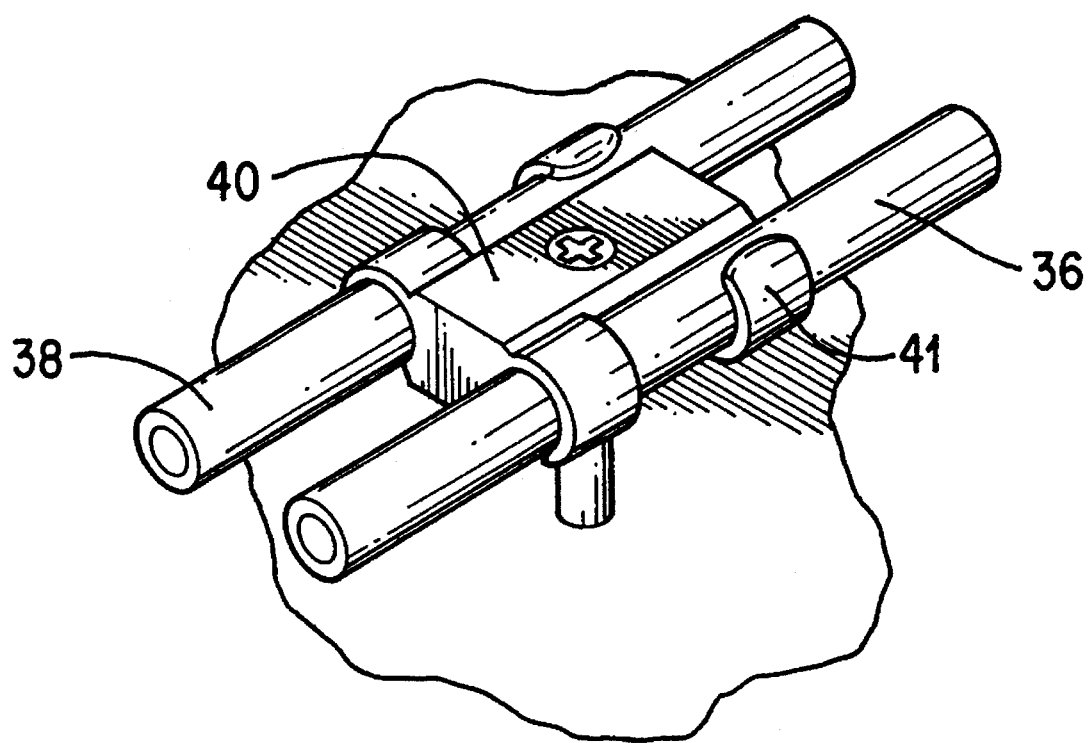
FIG. 10 illustrates a retaining clip for a sample line and electronic line from an OVA.

Cable 38 and sample line 36 are secured to the side of data terminal 22 by any suitable means, such as retaining clip 40, shown in FIGS. 4 and 10. The retaining clip 40 in the described embodiment is available from McMaster-Carr of Santa Fe Springs, Calif. as Pan No. 7429K42. As shown in FIG. 10, cable 38 and sample line 36 are clipped into the arched portions 41 of retaining clip 40.

Figure 5:
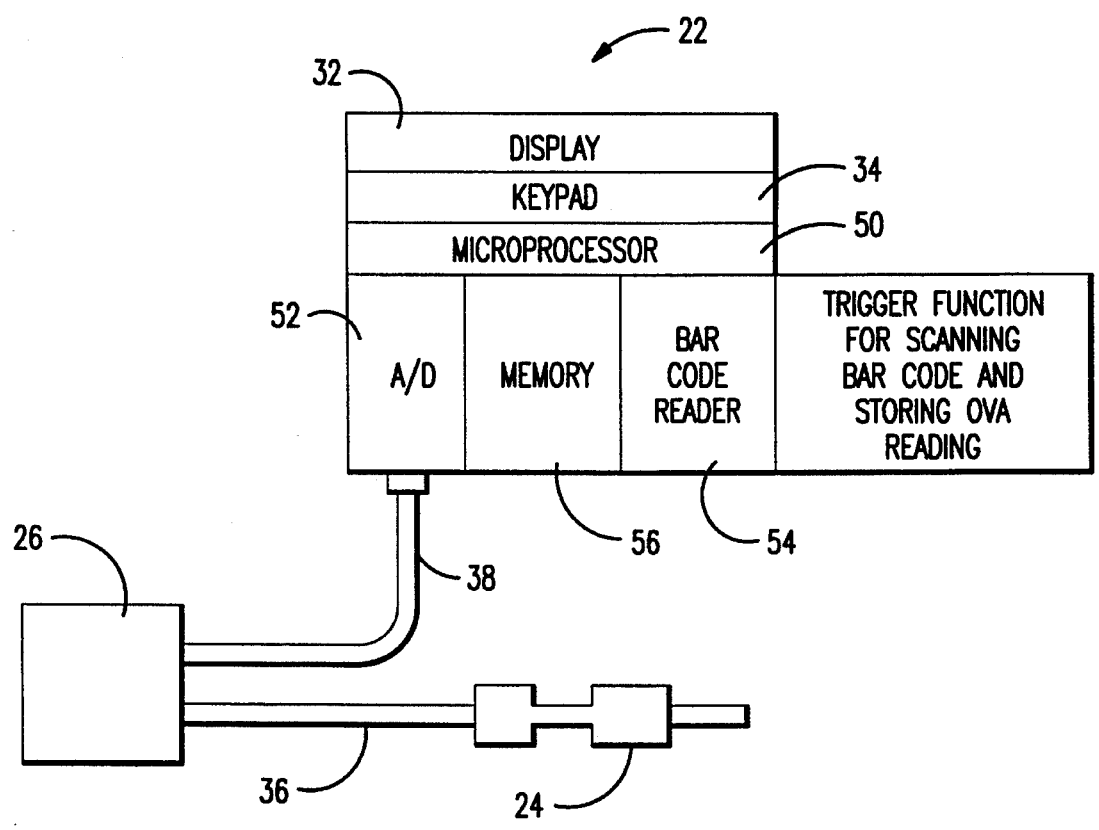
FIG. 5 is a block diagram illustrating some of the functions of the data terminal.
Figure 6:
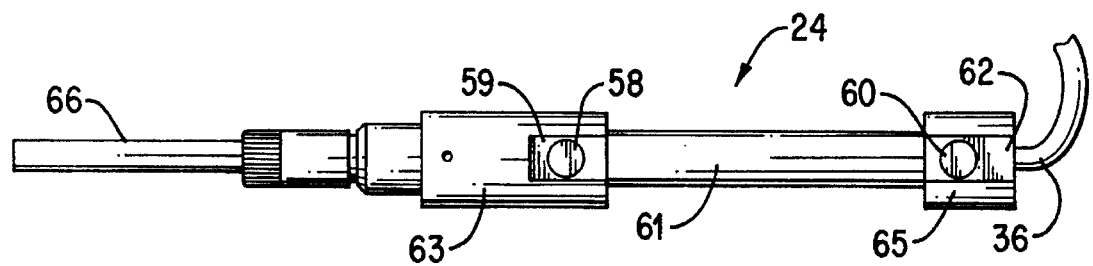
FIG. 6 is a top view of the probe shown in FIG. 2.
Figure 7:
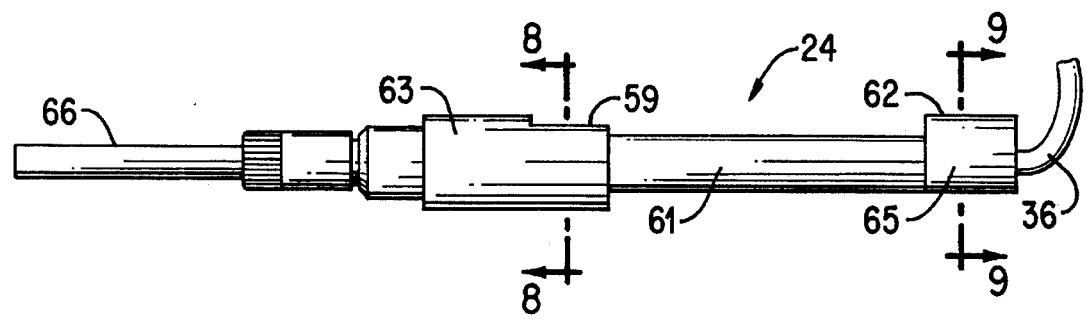
FIG. 7 is a side view of the probe shown in FIG. 6.
Figure 8:
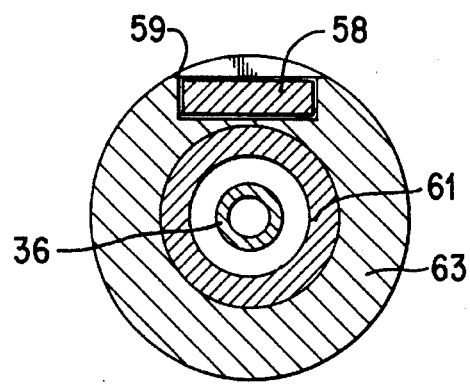
FIGS. 8 and 9 are sectional views taken along lines 8—8 and 9—9 of FIG. 7, respectively.
Figure 9:
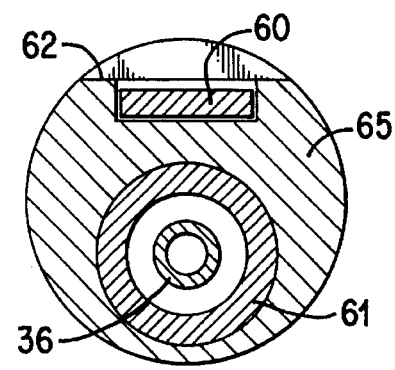

As shown in FIG. 5, the data terminal 22 includes an A/D converter 52 for convening the analog electric signal received from the OVA 26 via cable 38 into a digital representation. The A/D converter 52 provides a continuous conversion or the analog OVA signal into a digital representation, which is made available to the microprocessor and the display. Providing microprocessor 50 with access to the digital OVA measurement value allows the inspector to store OVA measurement values during an inspection by pressing the trigger 27 of data terminal unit 22. Pressing the trigger 27 (usually for the second time) causes microprocessor 50 to read the digital OVA measurement value from the A/D converter 52 and write this value to memory 56. (A first pressing of trigger 27 may cause barcode reader 54 to read a bar code into memory, and thereby identifying the release point). The function that pressing of the trigger causes is dependent on which screen is displayed or where in the inspection process the trigger is pulled. At the beginning of inspection of each component, pressing the trigger 27 causes the barcode reader to scan the component's bar code to allow the data terminal to verify that the correct component is being inspected. After the component has been verified as being correct when the inspector is actually inspecting the component by inputting the drip rate and measuring the OVA reading (described below under the OVA screen, FIG. 12J), pressing the trigger 27 causes the OVA reading to be read in and stored in memory 56.

Figure 13:
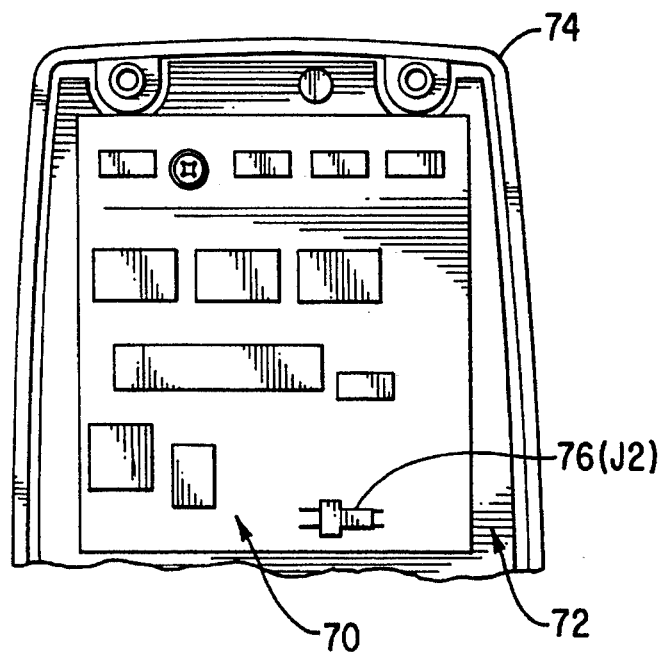
FIG. 13 is an interior view of the CPU/base assembly of the data terminal.
Figure 14:
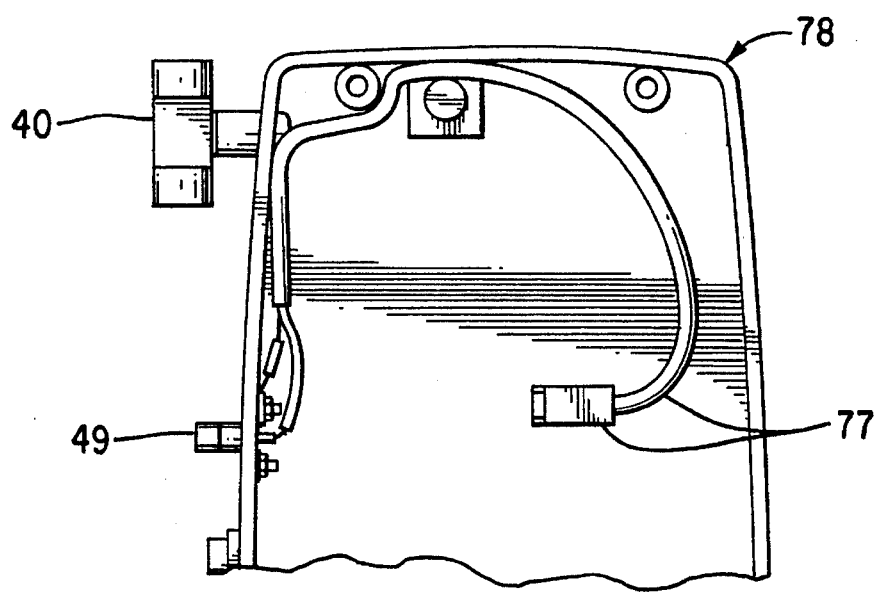
FIG. 14 is an interior view of the scanner/keyboard assembly of the data terminal.
Figure 15A:
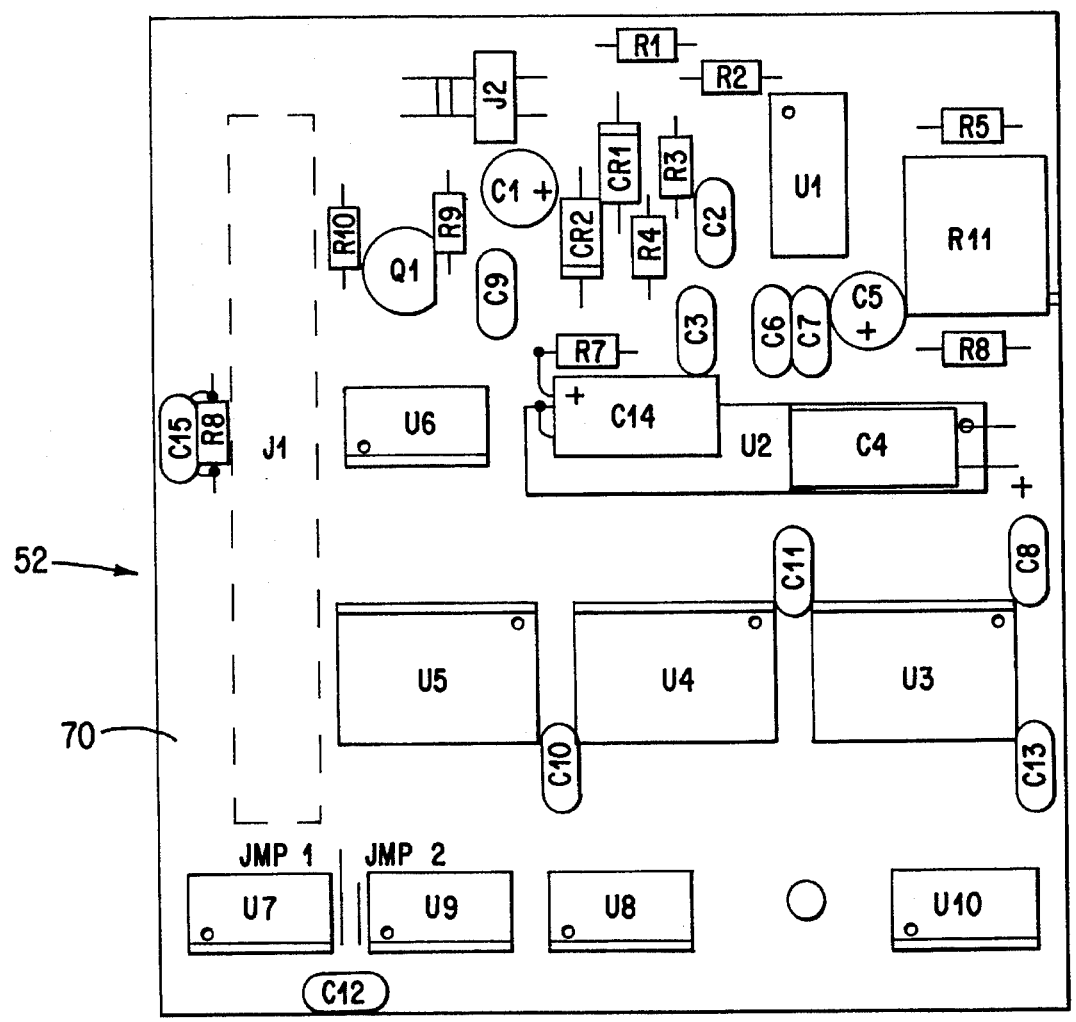
FIGS. 15A and 15B are top and side views respectively of the daughter board for the A/D converter.
Figure 15B:
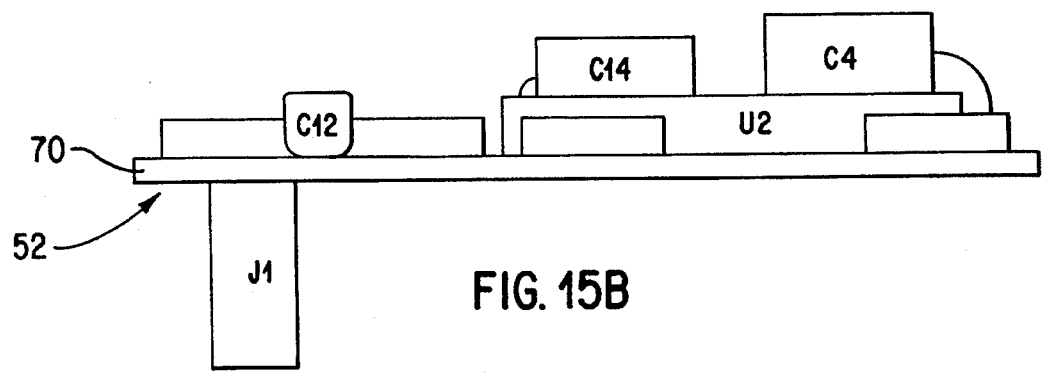

The illustrated data terminal unit 22 may be separated into a CPU/base assembly 74 (the lower portion of the data terminal) and a scanner/keyboard assembly 78 (the upper portion of the data terminal). The CPU/base assembly includes a mother board 72 that holds the microprocessor 50 and memory 56. FIG. 13 shows an interior view of the CPU/base assembly 74, with a daughter board 70 connected to the mother board 72. FIG. 14 shows an interior view of the scanner/keyboard assembly 78. The scanner/keyboard assembly 78 includes the barcode scanner or reader 54, the display 32 and the keypad 34.

As shown in FIGS. 13–16, A/D converter 52 includes an A/D converter integrated circuit (U2 in FIGS. 15–16), and other circuitry. The A/D converter 52 may use, for example, a Maximum MAX 190 integrated circuit as U2 for performing the analog to digital conversion process. In the preferred embodiment shown in FIGS. 13–16, the A/D converter 52, including the A/D integrated circuit (U2) and the related circuitry, is disposed on the daughter board 70 that is inserted into an internal memory expansion slot located on the mother board 72. To connect daughter board 70 to mother board 72, connector J1 (FIG. 15) on daughter board 70 is inserted into a memory expansion slot connector of the mother board 72.

The digital representation of the OVA measurement is connected from the outputs DBO–DB7 (FIG. 16) of the A/D converter 52 and other signals to the microprocessor 50 and memory 56 on the mother board via the connector J 1, which is connected to the memory expansion slot on the mother board. The analog input terminal 49, which receives the analog voltage signal from the OVA 26, is connected to connector 77 located within scanner/keyboard assembly 78. Connector 77 is connected to connector 76 (J2 of FIGS. 15–16) on the daughter board 70 prior to reassembling assemblies 74 and 78 of the data terminal unit 22. The connection of connectors 76 and 77 supplies the analog signal (AIN-1, FIG. 16) received on the input terminal 49 (from the OVA) to the A/D converter 52 located on daughter board 70. Connectors 76 and 77 may be any conventional electrical connectors. By utilizing the internal expansion slot of data terminal 22, all electrical components of the data terminal 22 (including the added A/D converter 52) are contained within the single handheld and portable package of the data terminal.

Figure 16A:
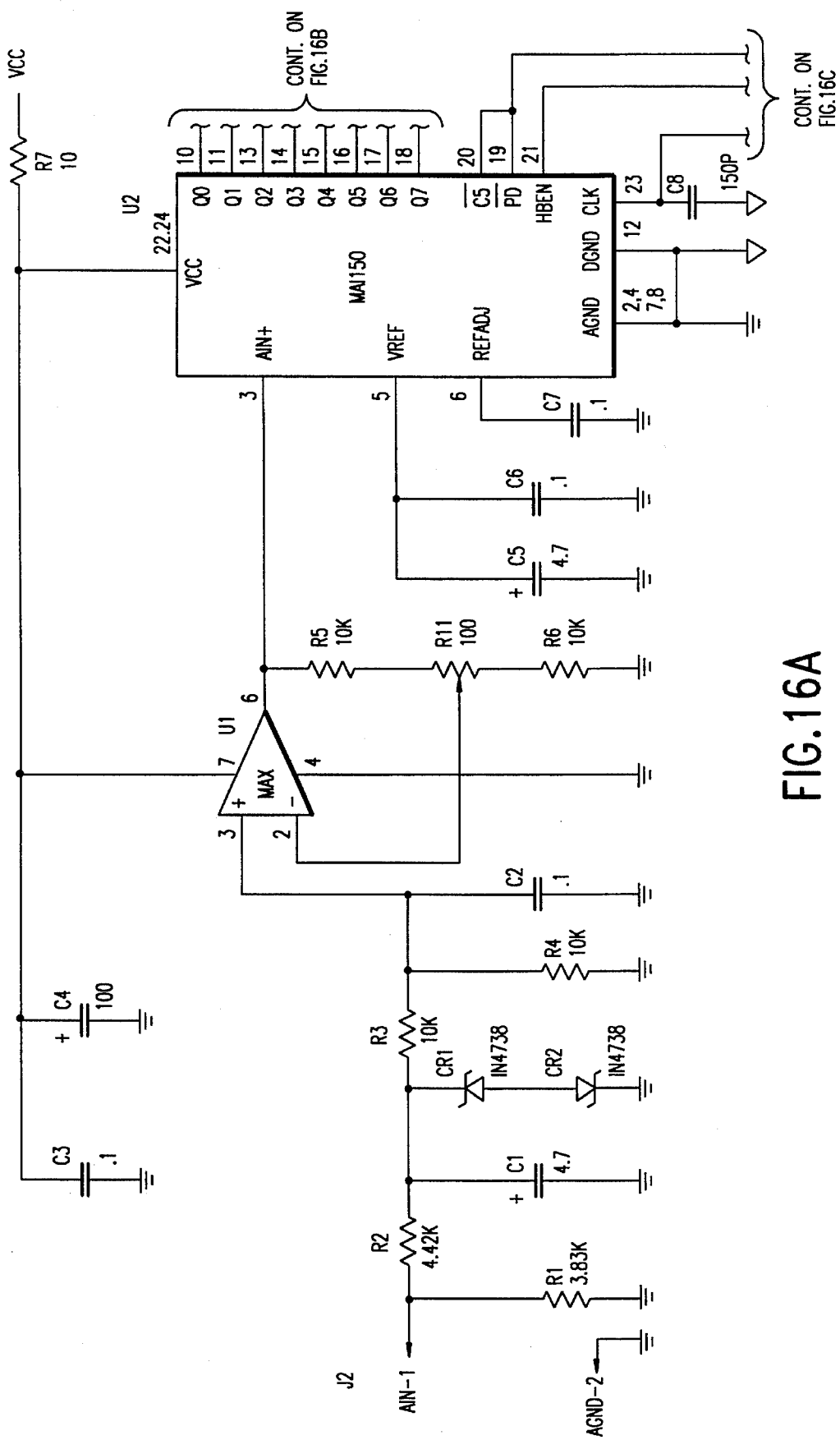
FIGS. 16A–16C comprise a schematic diagram of a preferred embodiment of the A/D converter.
Figure 16B:
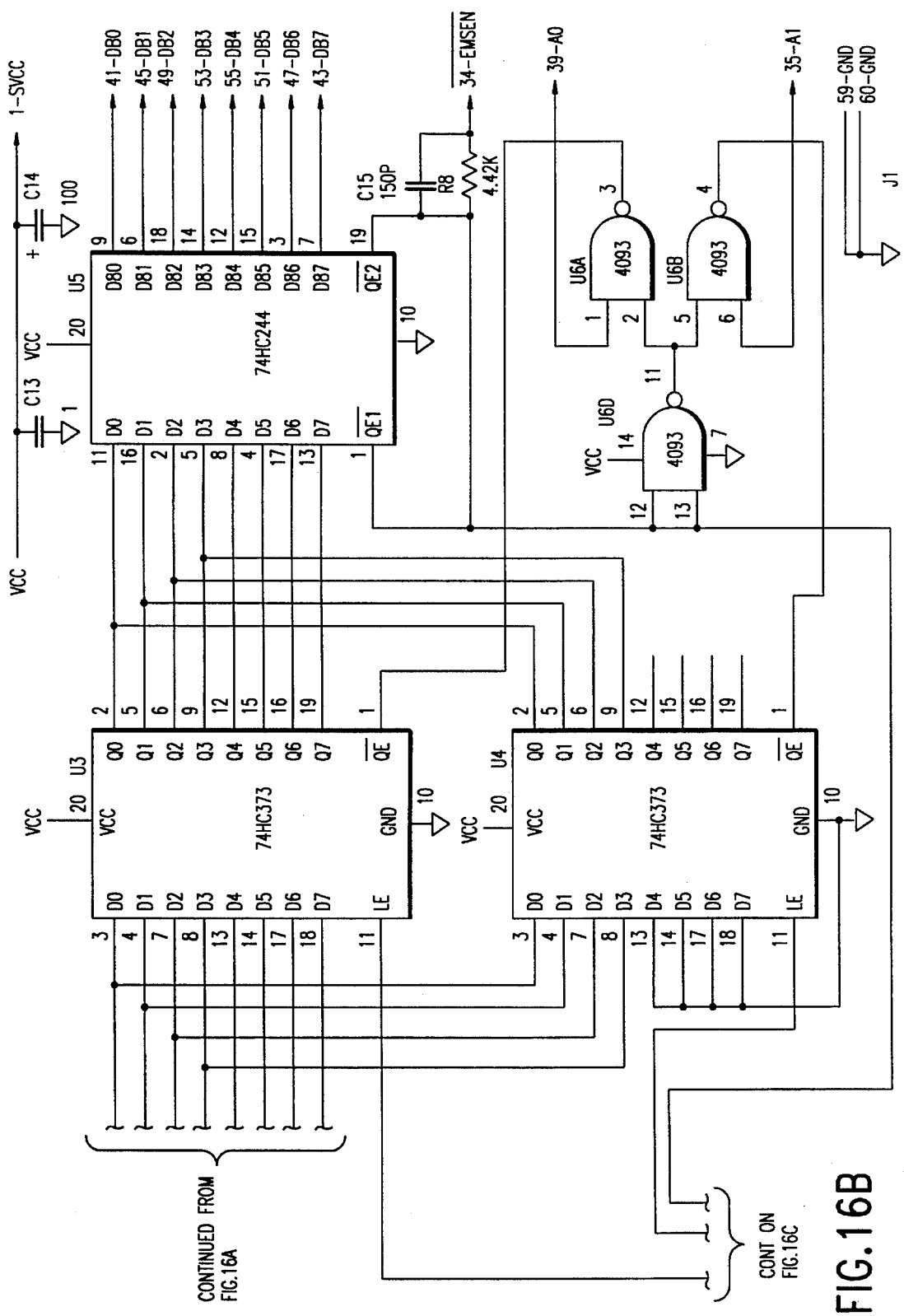
Figure 16C:
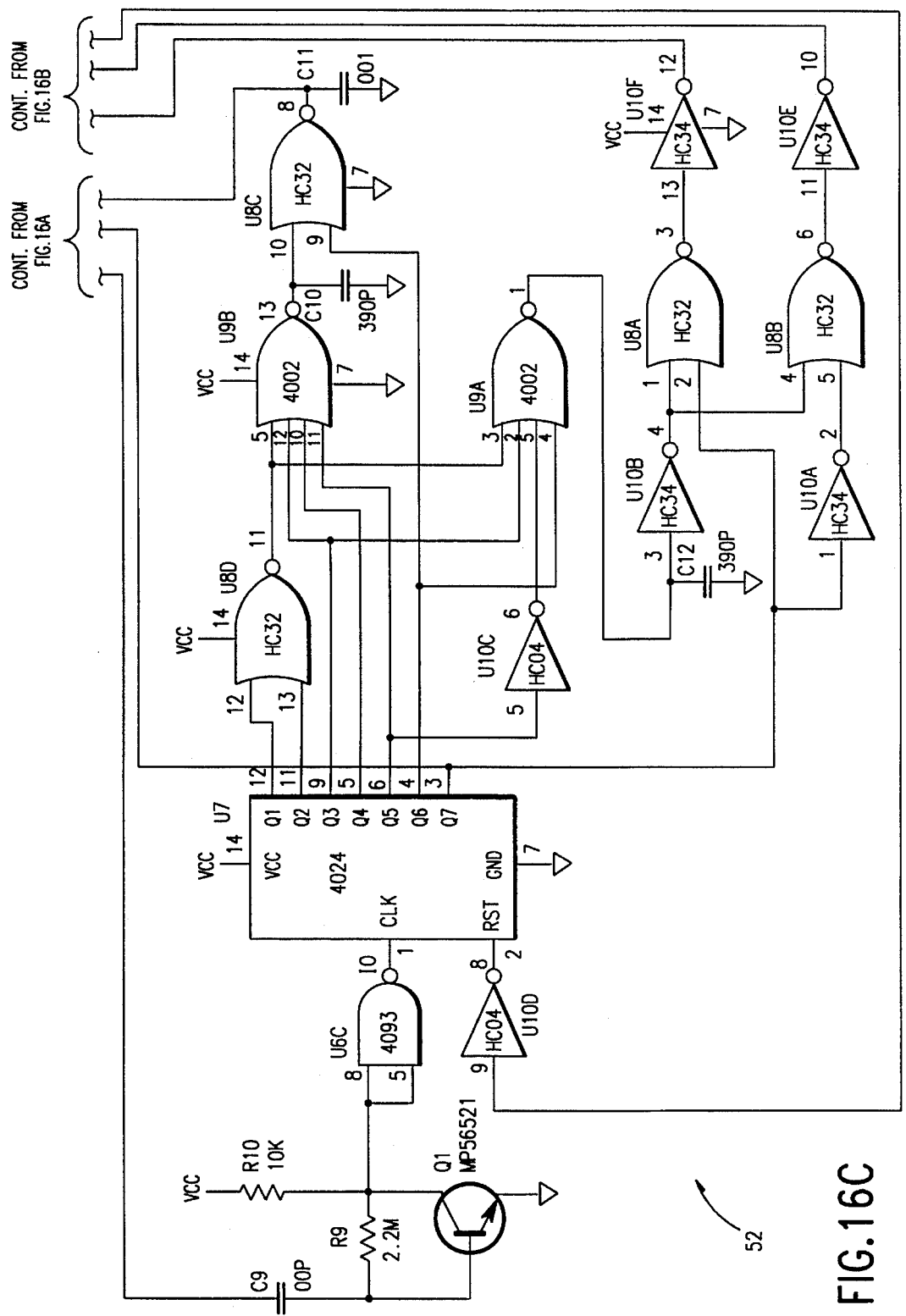

FIG. 16 is a schematic diagram of a preferred embodiment of the A/D converter 52 of the invention. The analog signal output by the OVA 26 is transmitted over cable 38 and connects to the A/D converter 52 via terminal 49 and connectors 76 (J2) and 77. The analog signal (AIN-1) is input to an operational amplifier (U1), and then is input to the 12-bit A/D converter integrated circuit (U2), where the analog signal is converted into a 12-bit digital signal. The digital signal is output as two bytes to latches (U3, U4). However, only four bits of the second byte are used. These two bytes are alternately output to data buffer/bus driver (U5). A ripple counter (U7) and other surrounding logic is employed as control circuitry to assist in coordinating the operation of the other components. The digital value is output as two bytes on the data output lines DB0–DB7 of U5.

Because the A/D converter 52 is inserted into the mother board's memory expansion slot, the mother board's full address and data busses are available to the A/D converter 52, and the microprocessor accesses the digital values by performing a memory access or read. The microprocessor believes it is reading a memory location in its expanded (extended) memory, and does not know it is an output of an A/D converter. The data for each measurement is obtained by the microprocessor 50 through two one-byte reads to obtain the 12 bits of data. Microprocessor 50 accesses the digital values by activating the EMSEN (extended memory select enable) signal, which causes the A/D integrated circuit to stop converting, and enables the bus driver U5 to output the current data onto the data bus. The address lines A0 and A 1 specify the two bytes (of the expanded or extended memory) output to the data bus for reading by the microprocessor 50. The signals EMSEN, A0 and A1 are output by the microprocessor in order to receive the digital value of an OVA reading. The control signal EMSEN, address signals A0 and A1, and the data lines DB0–DB7 are connected between the A/D converter 52 and the mother board's data, control and address busses (and thus, connected to the microprocessor and the memory) via the J1 connector between the daughter board and the mother board.

In accordance with the operational software program, after reading the 12 bits of data from the A/D converter, the microprocessor stores the digital data in memory 56. The microprocessor then converts the 12-bit value, which represents a value between zero and five volts (with five volts being the maximum input to the A/D integrated circuit), into the corresponding OVA measurement of hydrocarbons in parts per million (PPM). Since 12 bits allow 4096 different digital values, the voltage input to the A/D integrated circuit is calculated as:

$$\text{Voltage} = \text{Binary Value} \times \frac{5 \text{ Volts}}{4096}$$

The PPM value is calculated as:

PPM=Antilog (Voltage)

The microprocessor then calls the display routine of the 3805 DCT (which is incorporated in the software of the 3805 DCT), to display the OVA reading in parts per million (PPM). The microprocessor may also compare the PPM value to maximum allowable values, and sound an audible alarm or buzzer if the maximum value is exceeded, or the value may be recorded in memory automatically or on the inspector's command by pulling the trigger. Ideally, the operational software program instructs the microprocessor to frequently and periodically read the digital value, convert the value into PPM, and display the value. The digital value should be read and displayed frequently enough to provide the inspector with a continuous and current display of the OVA measurement, and provide a continuous display in addition to the other tasks being performed by the microprocessor. It should be understood that instead of reading the value from the A/D converter and converting the value into PPM under the microprocessor control, the digital value could be periodically latched or read into a buffer or memory circuits, and then converted to PPM using only hardware, such as a programmable logic array (PLA) to more rapidly read and display the digital values, and to prevent overburdening the microprocessor.

In addition, the A/D converter 52 is designed to appear the same electrically to the OVA as the analog meter so as to not affect the accuracy of the electrical signal output by the OVA. Thus, the resistance of the A/D converter is approximately 3000Ω, the same resistance as the analog meter normally used with the OVA.

The data terminal 22 is programmed with software that is executed by the microprocessor 50, that guides the inspector through inspection of release points, stores the collected data for later transfer to the main computer, and provides repair information to the inspector, as appropriate. The software may also control the reading of values output by the A/D converter and the display of the sensed emission concentration on the display 32. Memory 56 may include a read only memory (ROM) and a random access memory (RAM). The software may be downloaded into RAM, or programmed into the ROM using the main computer. Alternatively, the software may be burned into an electrically erasable programmable read only memory (EEPROM) or other memory device residing in the data terminal 22 as part of memory 56 using an EEPROM programmer. The software program is then executed by microprocessor 50.

During inspection, probe 24 receives emissions samples and transmits the samples to the OVA 26 via gas sample line 36. The OVA measures the total organic vapor concentration in the sensed vapor samples and transmits a representative analog electrical signal to the data terminal 22 via cable 38. A/D converter 52 continuously converts the analog emissions signal to a digital representation and makes the converted data available to microprocessor 50 and display 32. Also during the inspection process, the microprocessor 50 executes the software, reads in the digital data from the A/D converter, and continuously updates the display screen 32 to continuously display the current value of the sensed emissions signal.

Data terminal 22 provides an audible warning tone to alert the inspector whenever the OVA reading exceeds an established regulatory emissions threshold or maximum. This alarm can be adjusted to be activated at different thresholds, usually measured in parts per million (PPM). This audible tone may be programmed to occur only during inspection of a component, but preferably is provided at any time that data terminal 22 is on. Continuous monitoring by data terminal 22 of the level of the OVA reading received from the A/D converter 52 is possible because the OVA 26 continuously sends an analog electrical signal to A/D converter 52, and A/D converter 52 continuously converts the received analog signal to a digital representation that is displayed on display 32, regardless of what other tasks the microprocessor may be performing.

The software stores and tracks information about the release points that are the subject of an inspection trip. This information can be grouped into information that is downloaded from the main computer into the data terminal 22 and inspection data that is collected on-site and then uploaded from the data terminal to the main computer.

The downloaded information is grouped for convenience into three files, each of which is a flat-file database file, having one or more records, each of which contains one or more fields of information. The first downloaded file is the INVENTORY file, each record of which contains information about a single release point.

The fields of the INVENTORY file are identified and briefly described in the following table.

| Field Name | Type | Width | Description |
|---|---|---|---|
| Comp_ID | N | 6 | Unique ID for component |
| Tag | N | 15 | Bar code number |
| Unit | C | 5 | Unit code |
| Process | C | 5 | Process code |
| Equipment | C | 12 | Equipment code |
| Comp_Type | C | 2 | Component type code |
| Sub_Type | C | 2 | Component sub-type code |
| Size | C | 5 | Size of component |
| Description | C | 40 | Describes component |
| Location | C | 40 | Describes location of component |
| Insp_Type | C | 1 | Holds inspection code (O = Original, R = Re-inspect, M = Monthly re-inspect) |
| Threshold | N | 6 | Value at which OVA reading is above the regulatory leak threshold |

In this table, "Type" indicates whether the field contains numeric (N) or character (C) data, while "Width" indicates the number of characters or digits allowed for the field. The Comp_ID provides a unique identifier for the component, so that each of the many hundreds or thousands of components in a large refinery can be distinguished from each other. The bar code number (typically a five digit number) on the bar code tag associated with the component is stored in the Tag field. The Unit, Process and Equipment fields are used to identify the general location of a component in a facility. The Unit field identifies the unit (e.g., Catalytic Cracking, Logistics, Utilities) in which the component resides. A Unit usually consists of many processes. Therefore, the Process field identifies which process (e.g., hydrogen treating, desulfurization) the component resides. Each process includes several pieces of equipment (e.g., storage tank, column, fuel gas scrubber). The Equipment field identifies the specific piece of equipment within the process and unit on which the component resides.

The component's type (e.g., valve, connector, pump, compressor, pressure relief device) is identified by the 2 character code in the Comp_Type field. The component type is further broken down into a sub type (e.g., gate valve, ball valve, flange, elbow, reciprocation compressor) and is identified by the 2 character code in the Sub_Type field. The size field is used to identify the size of valves only. The size of the valve corresponds to the diameter of the piping it is servicing, and is usually expressed in inches.

A 40 character textual description of the component is contained in the Description field and describes the physical characteristics of the component (e.g., 2" quarter turn gated valve, yellow), and a 40 character description of where the component's location on a piece of equipment (e.g., north side U-100, 10 feet up) is contained in the Location field. The value of organic vapor concentration above which the component is considered to be seriously leaking is identified in the Threshold field. Finally, the type of inspection that the component is to receive, or has received, on the present inspection is identified in the Insp_Type field.

Questions for the inspector are contained in the QUESTION file. These questions may reflect information that is unique to a particular plant being inspected, and that is not normally included in the requests for information displayed to the inspector by display 32. The QUESTION file has one record for each question, with two fields. The Question field contains a 40 character textual question, while the Comp_Type field contains the component type (using the same code as the Comp_Type field in the INVENTORY file) to which the question corresponds.

The third downloaded file is the CODES file, in which each record corresponds to a code. The CODES file comes from the codes database file that is part of the main operating program on the main computer. The CODES file is used so that proper names and not codes are displayed on the data terminal. For example, the data terminal would display the proper name "GATE VALVE" and not the corresponding code "GV", when a gate valve is being inspected. The CODES file is downloaded from the main computer to the data terminal prior to each inspection so that deletions or modifications to Unit, Process, Equipment, Comp_Type, Sub_Type, Repair Attempt and Leak Location codes made on the main computer are accounted for by each data terminal. Each code is identified by a 5 digit type code, contained in the Code_Type field, and has associated with it 40 characters of text, contained in the Full_Text field. The third field is the Comp_Type field (containing the same component type code as in the INVENTORY file), which is only used for the minimization repair and part leaking codes.

As the inspector inspects each component or release point, a record is created for that component that contains the collected data, and selected fields from the corresponding record in the INVENTORY file. This record is included in a file to be uploaded to the main computer. This uploaded file is the INSPECTION file. The fields of the INSPECTION file are identified and briefly described in the following table.

| Field Name | Type | Width | Description |
|---|---|---|---|
| Comp_ID | N | 6 | Unique ID for component (same as INVENTORY file) |
| Threshold | N | 6 | Threshold for serious leak (same as INVENTORY file) |
| Insp_Type | C | 1 | Inspection type (same as INVENTORY file) |
| Inspector | C | 11 | Name of inspector who inspected this component |
| Insp_Dt | C | 8 | Date of original inspection |
| Insp_Time | C | 5 | Time of original inspection (military) |
| Leak_PPM | N | 6 | Original OVA look rate |
| Leak_Drp | N | 3 | Original drip rate (drips per minute) |
| Mi_Dt | C | 8 | Date of minimization repair |
| Min_Time | C | 5 | Time of minimization repair |
| Min_Lk_PPM | N | 6 | OVA leak rate after minimization repair |
| Min_Lk_DrP | N | 3 | Drip rate after minimization repair |
| Part_Lking | C | 2 | Code for part of component leaking |
| Added | L | 1 | Mark to ignore inspection data and consider this a new component |
| Modify | L | 1 | Mark indicating that component information needs to be updated |
| Retagged | L | 1 | Mark indicating that a new tag was placed on component |
| Deleted | L | 1 | Mark indicating that component no longer exists |
| New_Tag | C | 15 | New tag number if added or retagged |
| Answer_1 | L | 1 | Answer to question 1 |
| Answer_2 | L | 1 | Answer to question 2 |

In this table, a "Type" of "L" indicates a logical character. The primary key for this file is the Comp_ID field, which contains the unique component identification taken from the INVENTORY file. To simplify processing of the data by the main computer, the Threshold field simply contains the same information as the corresponding field in the INVENTORY file. The Insp_Type field indicates the type of inspection actually conducted. The inspector who inspected the component is identified in the Inspector field. This information is collected from the inspector at the beginning of the inspection trip, and is automatically placed in each record on that trip. Similarly, the inspection date and time (Insp_Dt and Insp_Time) are automatically collected from the data terminal's internal clock and placed in the record. The data terminal's clock and calendar are updated to correspond to main computer's clock and calendar during each download. The OVA leak rate first detected for the component is identified in pans per million in the Leak_PPM field, and the original drips per minute (if the component is dripping liquid) is identified in the Leak_Drp field.

If the inspector makes a minimization repair on-site in response to a prompt from the software, data concerning the date and time of the repair is stored in the Min_Dt and Min_Time fields, respectively, and the OVA leak rate and drips per minute after the minimization repair is made are stored in the Min_Lk_PPM and Min_Lk_Drp fields, respectively. If there is a leak that is not repaired upon detection, the inspector may identify the component that is leaking by selecting from a menu of pans of the component (e.g., valve stem, flange, grease fitting). The selections provided in the menu are downloaded with the CODES file.

If the component to which the record pertains was added during the present inspection trip (so that no information about it was present in the main computer or downloaded to the data terminal before the inspection trip), the Added field contains a flag indicating that the component is new. If the component's inventory is incorrect (e.g., the size is listed as 1"but actually is 2"), so that the data in the main computer associated with the component needs to be updated, the Modify field contains a flag indicating that the main computer should so update the data. If the inspector retagged the component (because, for example, the old tag had become damaged and unreadable), the component needs to have its new tag number stored in the main computer in place of the old tag number. The Retagged field would therefore contain a flag indicating that action. If the component no longer exists (e.g., the component was removed during maintenance) a flag is set in the Delete field to indicate that the component's information should be deleted from the main computer. If the component is a new component or was retagged, the new tag number is contained in the New_Tag field. Finally, the inspector's logical answers (yes/no) to each question asked by the software about this component during the inspection is stored in fields Answer_1, Answer_2, etc.

The software displays a number of successive screen displays to guide the inspector through the inspection process. Each screen provide information, instructions, and/or questions for the inspector. In response, the inspector may take action (such as scanning a tag or attempting a repair), provide data (such as a yes/no response to a question, identify a part), or select an option. The software's logical flow is illustrated in the flow chart shown in FIGS. 11A–11E.

The display 32 of the data terminal 22 can display 8 rows of 20 columns of characters. As discussed above, the hydrocarbon concentration sensed by the OVA and digitized by the A/D converter is continuously displayed in the first row of the display 32. The remainder of the display rows are used by the software to communicate with the inspector. FIGS. 12A–12N illustrate the various screen displays produced by the software. In each screen (other than the Upload/Download menu, which presumptively is accessed only when the inspector is off-site) the first row is illustrated as showing OVA:999999, indicating that the hydrocarbon concentration, in ppm. is displayed in 6 digits.

The software may be coded in the conventional manner (such as using the "C" programming language) and downloaded into the memory 56 before an inspector begins an inspection trip.

Figure 11A:
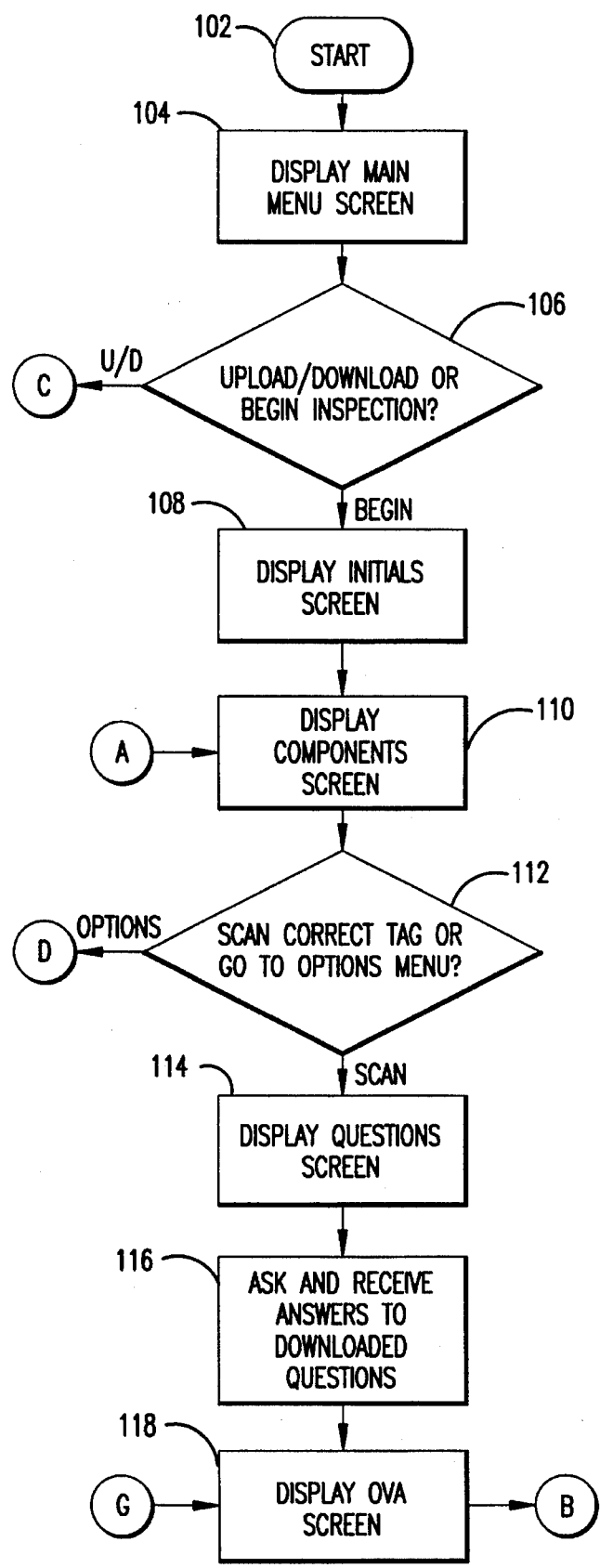
FIGS. 11A–11E are flow charts illustrating the operation of the software that guides an inspector through an inspection.
Figure 11B:
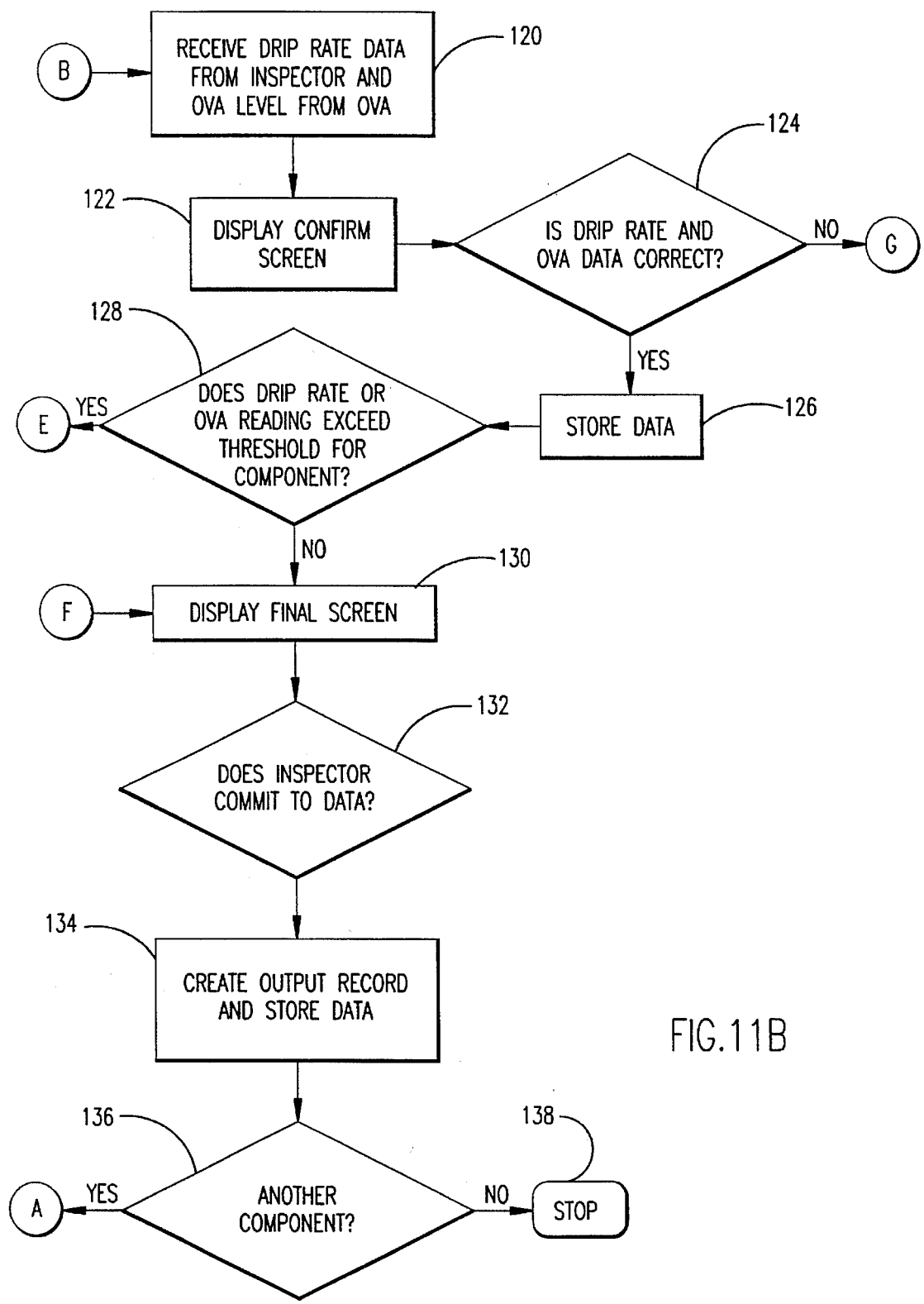
Figure 11C:
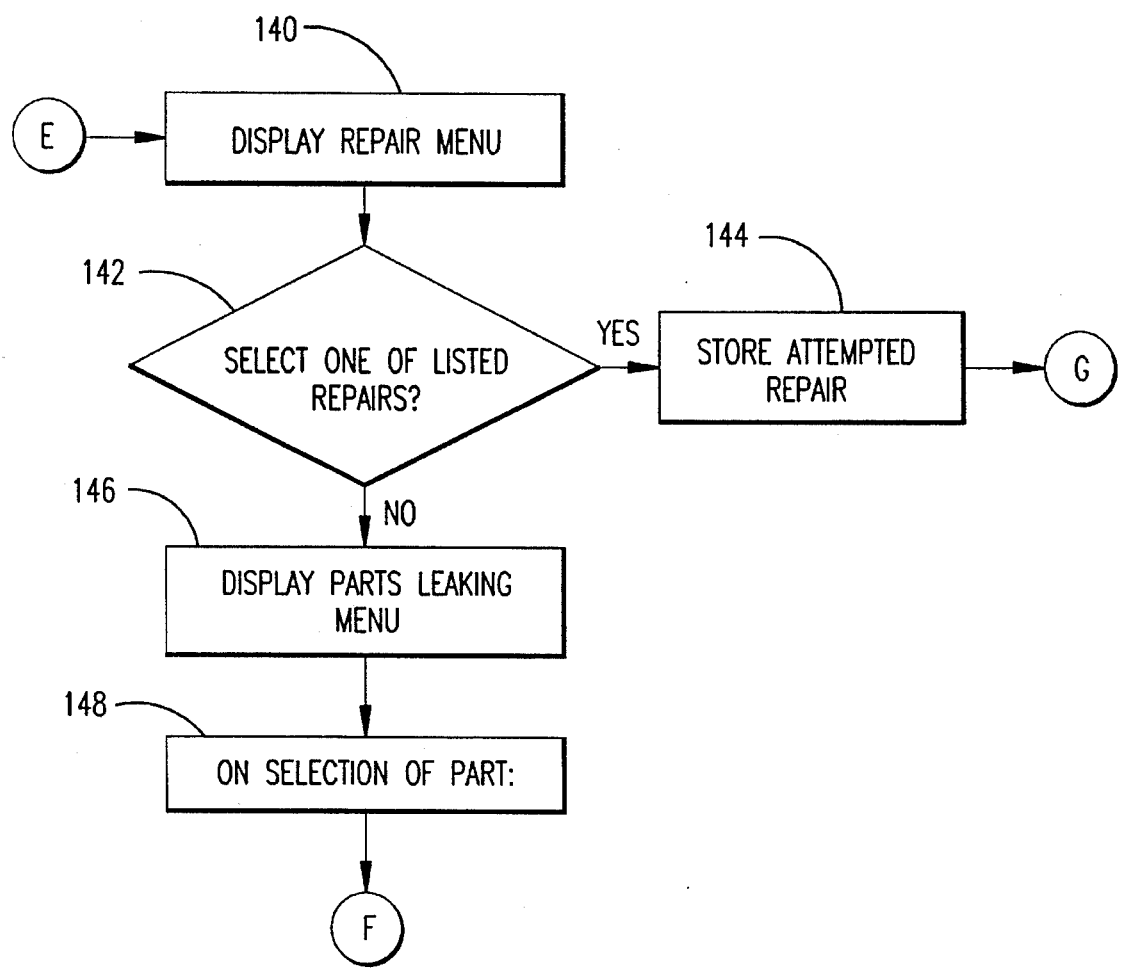
Figure 11D:
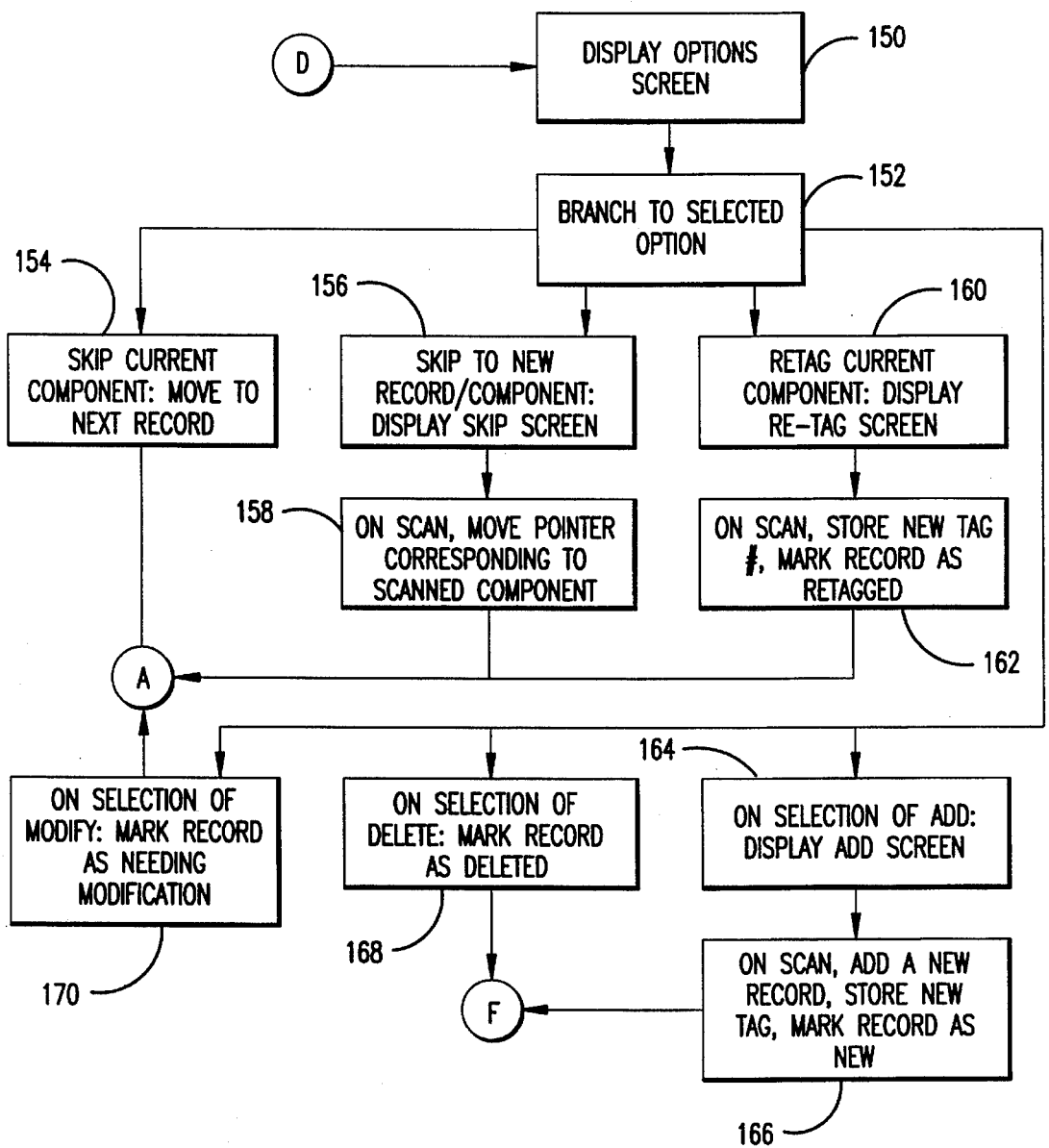
Figure 11E:
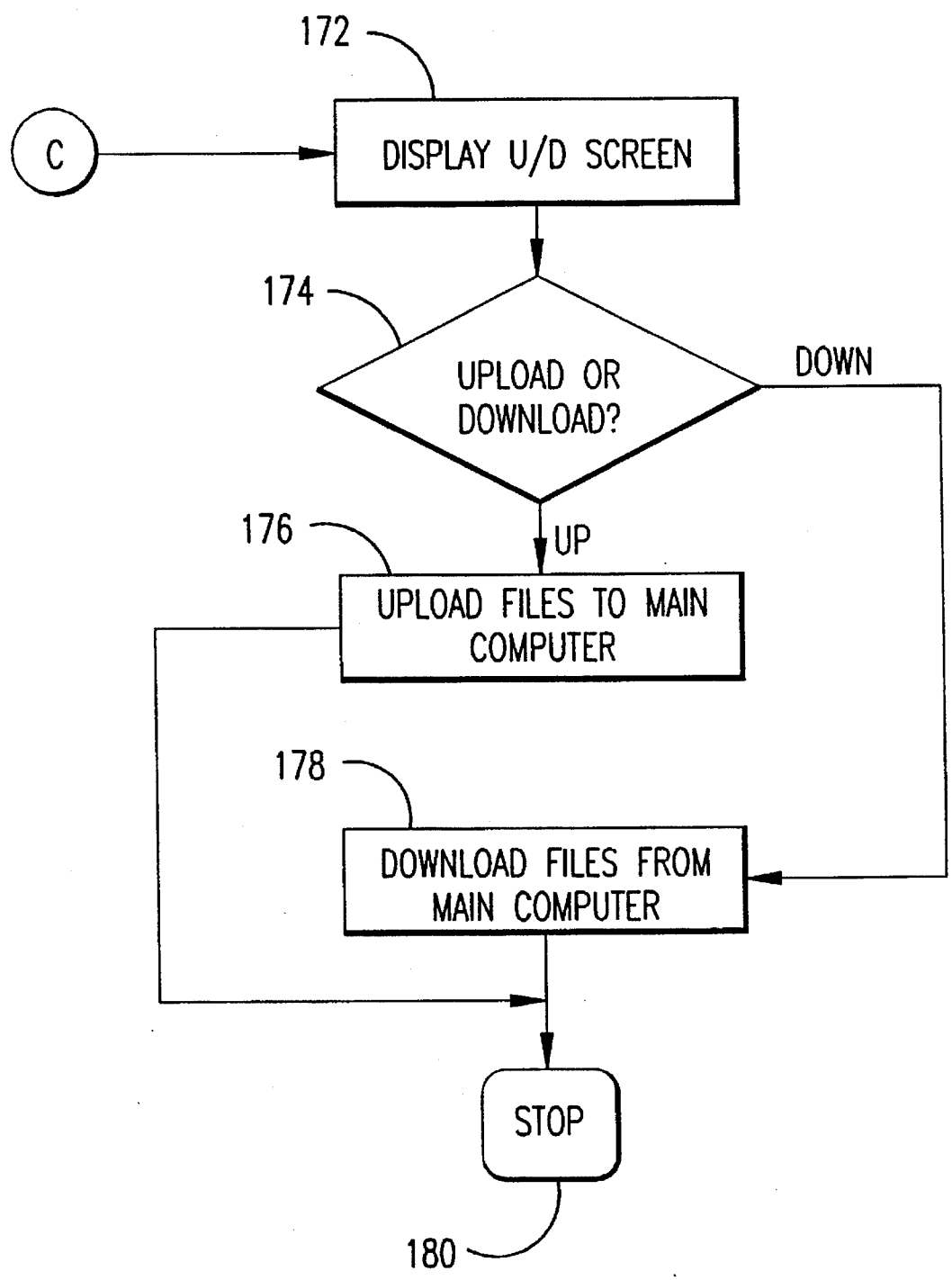

The inspection process begins at block 102 (shown in FIG. 11A). In block 104, the main menu screen (FIG. 12A) is displayed, in which the inspector is prompted to select the option of beginning an inspection or uploading/downloading data from the main computer.

If, at block 106, the inspector selects the option of upload/download, the program advances to block 172, where the program displays the Up/Download Menu screen (FIG. 12F). If, at block 174, the inspector chooses to download, the program advances to block 178, where the INVENTORY, QUESTION, and CODES files are downloaded from the main computer. If the inspector chooses to upload at block 174, the program advances to block 176, where the INSPECTION file is uploaded to the main computer. After either block 176 or 178, the program stops execution.

If, at block 106, the inspector selects the option of beginning inspection (by any conventional means, such as hitting the "1" key or scrolling the cursor in the display to the row containing the "Begin Inspecting" characters, and pressing an "Enter" key), the software progresses to block 108, the Initials screen (FIG. 12B) is displayed.

In response, the inspector enters his or her initials using keypad 34. The microprocessor then adjusts the pointer to the record for the first component (the first record). The record pointer identifies which record/component is displayed in the Components screen and identifies the "current" component. The component description is displayed as a component screen (an example of a Component screen is in FIG. 12C) that includes the various fields for this (the current) component, including those fields that have been downloaded to the data terminal 22. The inspector may scroll up or down to view all of the fields for the current component, and the displayed fields are in text or proper name format rather than the codes for easier identification. These fields include the equipment; the component type; the component size (field Size from the INVENTORY file); the description of what the component is (field Description from the INVENTORY file); the location (field Location); the process (field Process); and the unit (field Unit).

As shown in block 112, the inspector may scan the tag identifying the current component if he wishes to inspect the current component, or instead may select an options menu if he wishes to do something other than inspect the current component. If the inspector chooses to inspect, the inspector scans the component's tag. Upon a correct scan (i.e., the scanned tag number matches the tag number contained in field Tag from the INVENTORY file for the current record) the software displays in block 114 the Question screen (FIG. 12D), in which the custom questions that were downloaded are displayed and the inspector inputs answers using the keypad 34 in block 116. Upon completion of the questions, the software displays in block 118 the OVA screen (FIG. 12J).

The inspector checks the component for drips and enters the drip rate. The inspector then observes the display 32 for the displayed value of the hydrocarbon concentration received from the OVA and locks the data into the data terminal (by, for example, pulling trigger 27) when the OVA reading (on the first line of the display 32) peaks. The software receives this input in block 120, then displays in block 122 the Confirm screen (FIG. 12K), which asks the inspector to confirm the values in block 124. If the values are correct, then in block 126 they are stored in fields Leak_PPM and Leak_Drp in the INSPECTION file record for this component. If the values are incorrect, the program returns to block 118, redisplaying the OVA screen for reentry of the values.

In block 128, the program compares the entered drip rate and OVA reading to the downloaded threshold values (field Threshold for the OVA reading from the INVENTORY file, and the drip rate threshold has a default of 3 drips per minute) for this component. If the drip rate and OVA reading are within their threshold values, the program advances to block 130, where it displays the final screen (FIG. 12N). In the final screen, the program displays information about the component, including the original and after-repair (if any) drip rate and OVA reading, and asks the inspector whether to commit the information to the INSPECTION file. If, in block 132, the inspector commits to the data, the data is written to an output record in the INSPECTION file.

The record pointer is then incremented to the next record/component in the INVENTORY file. If, in block 136, the program determines that another record/component exists, the program returns to block 110 and the process is repeated for this next component.

In block 132, if the inspector chooses not to commit the information to the INSPECTION file (because it is not correct), then the data are erased, and therefore not written to an output record in the INSPECTION file, and the program returns to block 110 to repeat the process for the current component/record because an error was made.

If, in block 128, the drip rate or OVA reading exceeds its threshold value, the program goes to block 140, where it displays the Repair menu (FIG. 12L), which shows a list of repair attempt options for this component type. FIG. 12O is an example of a Repair menu. The repair attempt options are dependent on the type of component being inspected. For example, for a valve, a repair option may be to tighten the packing or to inject grease; for a connector, to tighten the fitting, etc.

In block 142, the inspector may select one of the repair options, and attempt the repair of the component. In block 144, the attempted repair is stored. Control is then passed back to block 118, where the OVA screen is again displayed so that the drip rate and OVA reading can be taken again and compared to determine if the repair was sufficient to cause the drip rate and OVA reading to be less than the thresholds. This loop is repeated until "No Repair Attempt Made", or the repair attempts were unsuccessful.

If no repair was attempted at block 142, then in block 146 the Part Leaking menu is displayed, which shows a list of locations on the component being inspected that can be leaking. The leak location selected is stored in memory (so that follow-up maintenance efforts may concentrate in that location), then the program proceeds to block 130 to display the final screen. For example, for a valve, a leak may occur at a valve stem, a grease fitting or an attaching connector, and the location of the leak is selected by the inspector from a menu.

If in block 112 the inspector chooses to go to the Options menu, the program proceeds to block 150 and displays the Options screen (FIG. 12E). The inspector may then select one of the six options, as shown in block 152. First, the inspector may choose to skip to the next component (i.e., the next record in the INVENTORY file), and therefore, in block 154, the pointer in the INVENTORY file is moved to the next record, and the next component becomes the current component.

Second, the inspector may skip to a new component. If so, then in block 156, the program displays the Skip screen (FIG. 12G). The inspector then scans in the tag of the component to which he wishes to skip. Upon completion of the scan, in block 158, the program moves the pointer in the INVENTORY file to the record corresponding to the scanned component, changing the current component to the new component.

Third, the inspector may choose to retag the current component. If so, the program goes to block 160, and displays the Re-tag screen (FIG. 12H). The inspector retags the component, then scans the new tag. Upon the successful scan of the new tag, in block 162, the program stores the new tag number (in the New_Tag field) and marks the component as retagged (in the Retagged field).

Fourth, the inspector may choose to modify the current record, for example, if the original inventory was recorded incorrectly. If so, in block 170 the program marks the record as needing modification.

After completing any of the first four options of block 152, the program proceeds to block 110 to display the components screen.

Fifth, the inspector may choose to add a new record/component to memory. If so, the program proceeds to block 164 and displays the Add screen (FIG. 12I). The inspector affixes a tag to the new component and scans the tag. Upon a successful scan, in block 166, the new tag number is stored (in field New_Tag), and the component is marked as being added to the inventory (in field Added).

Finally, the inspector can choose to delete a component from the inventory. If so, the program proceeds to block 168, where the program marks the component as being deleted (in field Deleted).

After either of the last two options, control is passed to bock 130, where the final screen is displayed.

The following example of an inspection trip further illustrates the operation of the hardware and software aspects of the invention.

At the beginning of each day an inspector will calibrate the data terminal with the OVA using calibration gasses, and checks the electronics. The data terminal unit is then placed in the charger/data transfer cradle so it may interface with the main computer (e.g. a personal computer). The data terminal is placed into the download mode by selecting the "upload/download" screen selection. At the main computer side, the operator makes various selections as to what types of components are to be inspected, selects a Unit, and a Process within the Unit, to be inspected. The pieces of equipment are displayed by codes and proper names and are selected and moved to a download screen. Once the operator has selected enough components for one day's worth of inspections (usually 250–500 components), the operator instructs the main computer to send (or download) these dam files on the components and other essential files into the data terminal.

Next, the inspector moves into the Unit and Process to be inspected. Beginning with the first component, the inspector locates and scans the component by pressing the trigger. If the scanned code corresponds to the current component, the inspector then reviews the component information for accuracy, and then proceeds through the inspection process and screen displays to inspect and record the data for this component as described above. For example, the inspector may inspect the component by pressing the trigger (a second time) to store the OVA reading in memory for comparison to the threshold, and observe and record a drip rate. If the inspector finds that the component is leaking or has an OVA reading above the threshold, the inspector will then attempt to implement one or more of the repairs on the component that are listed on the repair menu. This repair is also recorded (selected). The component would then be retested and another repair attempted and recorded, until the component passes or "No Repair Attempt Made" is selected. If "No Repair Attempt Made" is selected (or if the component passes), then the leak location is selected from a location list for the current component to record the leak location. Once this information is recorded, the initial and final leak rates, the repair attempts made and the leak location are displayed at the Final screen. If this information is correct, the inspector commits this inspection record to the inspection file contained in the data terminal, and the next component to be inspected is displayed on the display. Similarly, the inspector would proceed to inspect and record information on the remaining components. Other steps may also be performed by the inspector, such as adding a new component, modifying the component, retagging the component, deleting the component, etc., as described above.

After completing inspection of all components, the data terminal is again placed in the charger/data transfer cradle and the files are uploaded to the main computer. The main computer then updates its records and generates daily operation reports.

What is claimed is:

1. Apparatus for taking a gas sample at a release point tagged with an identification tag having a scannable identification code thereon, comprising:

a gas probe having a front mounting portion and a rear mounting portion spaced from said front mounting portion;

a gas analyzer coupled to said probe, said gas analyzer analyzing the gas sample received from said probe and generating a concentration signal representative of the concentration of a component of the gas sample;

means for scanning the identification tag and providing an identification code signal representative of the identification code;

means for storing said identification code signal and said concentration signal;

a display on which said concentration signal can be continuously displayed; and a data terminal housing said scanning means, said display and said storing means, said data terminal having a front mounting pad selectively engageable with said front mounting portion and a rear mounting pad selectively engageable with said rear mounting portion, said probe being disposed in an operative orientation when said front mounting portion is engaged to said front mounting pad ad said rear mounting portion is engaged to said rear mounting pad, and said front mounting portion disengaging from said front mounting pad preferentially to said rear mounting portion disengaging from said rear mounting pad in response to a force applied to said probe, and said display and said scanning means being disposed on said data terminal so that said display is visible to a user while scanning the identification tag and while taking a sample when said probe is mounted to said data terminal in said operative orientation.

2. The apparatus of claim 1 wherein the concentration signal generated by the gas analyzer is an analog signal, and further comprising an A/D converter coupleable to the gas analyzer and converting said analog concentration signal to a digital concentration signal, said A/D converter being housed in said data terminal and coupled to said storing means.

3. The apparatus of claim 2 wherein said data terminal further comprises an internal expansion slot and wherein said A/D converter is coupled to said internal expansion slot.

4. The apparatus of claim 2 wherein said A/D converter includes an integrated circuit for converting analog signals to a digital representation, said A/D converter being mounted on a daughter board located inside said data terminal.

5. The apparatus of claim 4 wherein said storing means and a means for processing are interconnected and mounted on a mother board located inside said data terminal, said daughter board connected to said mother board thereby connecting said A/D converter to said processing means and said storing means.

6. Apparatus for taking a gas sample at a release point tagged with an identification tag having a scannable identification code thereon, and analyzing said gas sample with a gas analyzer that receives the gas sample and generates a concentration signal representative of the concentration of a component of the gas sample, comprising:

a gas probe fluidically coupled to the gas analyzer, said probe having a front mounting portion and a rear mounting portion spaced from said front mounting portion;

means for scanning the identification tag and providing an identification code signal representative of the identification code;

means for storing said identification code signal and said concentration signal;

a display on which said concentration signal can be continuously displayed;

a data terminal housing said scanning means, said display, and said storing means, said data terminal having a front mounting pad selectively engageable with said front mounting portion and a rear mounting pad selectively engageable with said rear mounting portion, said probe being disposed in an operative orientation when said front mounting portion is engaged to said front mounting pad and said rear mounting portion is engaged to said rear mounting pad, and said front mounting portion disengaging from said front mounting pad preferentially to said rear mounting portion disengaging from said rear mounting pad in response to a force applied to said probe, and said display and said scanning means being disposed on said data terminal so that said display is visible to a user while scanning the identification tag and while taking a sample when said probe is mounted to said data terminal in said operative orientation.

7. A collection system for monitoring fugitive emission sources, comprising:

identification codes disposed at each fugitive emission source for identifying each fugitive emission source;

a handheld data terminal including:
     a code reader for reading said identification codes and providing a
     signal representative thereof;
     a display for displaying information to a user;
     a memory for storing information; and
     data processing means coupled to said memory and said display for processing information based on one or more programs stored in said memory;

an emission receiving probe for receiving fugitive emissions from the fugitive emission sources, said probe having a front mounting portion and a rear mounting portion spaced from said front mounting portion; and an emissions analyzer coupled to said probe and said data terminal for analyzing fugitive emissions received by said probe and generating an emissions signal representative thereof, said data terminal having a front mounting pad selectively engageable with said front mounting portion and a rear mounting pad selectively engageable with said rear mounting portion, said probe being disposed in an operative orientation when said front mounting portion is engaged to said front mounting pad and said rear mounting portion is engaged to said rear mounting pad, and said front mounting portion disengaging from said front mounting pad preferentially to said rear mounting portion disengaging from said rear mounting pad in response to a force applied to said probe, and said display and said code reader being disposed on said data terminal so that said display is visible to a user while reading the identification code and while taking a sample when said probe is mounted to said data terminal in said operative orientation.

8. Apparatus for taking a gas sample at a release point tagged with an identification tag having a scannable identification code thereon, and analyzing said gas sample with a gas analyzer that receives the gas sample and generates a concentration signal representative of the concentration of a component of the gas sample, comprising:

a gas probe fluidically coupled to the gas analyzer, said probe having a front mounting portion and a rear mounting portion spaced from said front mounting portion;

means for scanning the identification tag and providing an identification code signal representative of the identification code;

means for storing said identification code signal and said concentration signal;

a data terminal housing said scanning means and said storing means and having a front mounting pad magnetically engageble with said front mounting portion and a rear mounting pad selectively engageable with said rear mounting portion, said probe being disposed in an operative orientation when said front mounting portion is engaged to said front mounting pad and said rear mounting portion is engaged to said rear mounting pad, and said front mounting portion disengaging from said front mounting pad preferentially to said rear mounting portion disengaging from said rear mounting in response to a force applied to said probe.

9. The apparatus of claim 8 wherein said front mounting portion includes a first probe magnet fixed to said probe and wherein said front mounting pad includes a first terminal magnet fixed to said data terminal, said first probe magnet being magnetically attracted to said first terminal magnet.

10. The apparatus of claim 9 wherein said rear mounting portion includes a second probe magnet fixed to said probe and wherein said rear mounting pad includes a second terminal magnet fixed to said data terminal, said magnets being disposed on said probe and said data terminal so that when said first probe magnet is aligned with said first terminal magnet, said second probe magnet is aligned with said second terminal magnet.

11. The apparatus of claim 10 wherein said second terminal magnet projects outward from its respective mounting surface, said second probe magnet is recessed inward from its respective mounting surface, the recess formed by said second probe magnet matingly receiving the projecting portion of said second terminal magnet when said second probe magnet and said second terminal magnet are brought together.

12. Apparatus for taking a gas sample at a release point tagged with an identification tag having a scannable identification code thereon, and analyzing said gas sample with a gas analyzer that receives the gas sample and generates a concentration signal representative of the concentration of a component of the gas sample, comprising:

a gas probe having a first end for receiving the gas sample and a second end fluidically coupleable to the gas analyzer and having a front mounting portion proximate to said first end and a rear mounting portion distal from said first end;

means for scanning the identification tag and providing an identification signal representative of the identification code;

means for storing said identification code signal and said concentration signal;

a data terminal housing said scanning means and said storing means having a front mounting pad selectively engageable with said front mounting portion and a rear mounting pad selectively engageable with said rear mounting portion, said probe being disposed in an operative orientation when said front mounting portion is engaged to said front mounting pad and said rear mounting portion is engaged to said rear mounting pad, and said front mounting portion disengaging from said front mounting pad preferentially to said rear mounting portion disengaging from said rear mounting pad in response to a force applied to said probe.

13. The apparatus of claim 12 wherein a first magnet is disposed on said front mounting portion of said probe and a complementarily polarized second magnet is disposed on said front mounting pad.

14. The apparatus of claim 12 wherein said rear mounting pad is recessed and said rear mounting portion projects outward whereby said rear mounting portion pivotally attaches to said rear mounting pad.

15. The apparatus of claim 14 wherein a first magnet is disposed on said rear mounting portion of said probe and a complementarily polarized second magnet is disposed on said rear mounting pad whereby said rear mounting portion of said probe is removably attached to said rear mounting pad.

* * * * *